United States Patent
Turnbull et al.

(10) Patent No.: US 10,710,963 B2
(45) Date of Patent: Jul. 14, 2020

(54) CHEMICAL COMPOUNDS

(71) Applicant: GlaxoSmithKline Intellectual Property (No. 2) Limited, Brentford (GB)

(72) Inventors: Philip Stewart Turnbull, Research Triangle Park, NC (US); Rodolfo Cadilla, Research Triangle Park, NC (US)

(73) Assignee: GlaxoSmithKline Intellectual Property (No.2) Limited (GB)

( * ) Notice: Subject to any disclaimer, the term of this patent is extended or adjusted under 35 U.S.C. 154(b) by 0 days.

(21) Appl. No.: 16/226,763

(22) Filed: Dec. 20, 2018

(65) Prior Publication Data

US 2019/0127326 A1    May 2, 2019

Related U.S. Application Data

(63) Continuation of application No. 15/358,458, filed on Nov. 22, 2016, now Pat. No. 10,196,353, which is a continuation of application No. 14/549,034, filed on Nov. 20, 2014, now Pat. No. 9,533,948, which is a continuation of application No. 13/941,911, filed on Jul. 15, 2013, now Pat. No. 8,957,104.

(60) Provisional application No. 61/748,874, filed on Jan. 4, 2013, provisional application No. 61/672,455, filed on Jul. 17, 2012.

(51) Int. Cl.
| | |
|---|---|
| *A61K 31/404* | (2006.01) |
| *C07D 209/42* | (2006.01) |
| *C07D 209/14* | (2006.01) |
| *C07D 401/06* | (2006.01) |
| *C07D 209/10* | (2006.01) |
| *C07D 209/08* | (2006.01) |

(52) U.S. Cl.
CPC .......... *C07D 209/14* (2013.01); *A61K 31/404* (2013.01); *C07D 209/08* (2013.01); *C07D 209/10* (2013.01); *C07D 209/42* (2013.01); *C07D 401/06* (2013.01)

(58) Field of Classification Search
None
See application file for complete search history.

(56) References Cited

U.S. PATENT DOCUMENTS

| | | | |
|---|---|---|---|
| 7,572,820 B2 * | 8/2009 | Turnbull | C07D 209/10 |
| | | | 514/361 |
| 8,026,262 B2 | 9/2011 | Turnbull et al. | |
| 8,957,104 B2 | 2/2015 | Turnbull et al. | |
| 9,533,948 B2 * | 1/2017 | Turnbull | C07D 209/08 |
| 9,902,694 B2 * | 2/2018 | Kaldor | C07D 209/42 |
| 10,196,353 B2 * | 2/2019 | Turnbull | C07D 209/08 |
| 2005/0222148 A1 | 10/2005 | Kim et al. | |
| 2005/0245485 A1 | 11/2005 | Lanter et al. | |
| 2005/0250740 A1 | 11/2005 | Lanter et al. | |
| 2005/0250741 A1 | 11/2005 | Lanter et al. | |
| 2012/0022096 A1 | 1/2012 | McKnight et al. | |

FOREIGN PATENT DOCUMENTS

| | | |
|---|---|---|
| WO | WO9943651 A1 | 9/1999 |
| WO | WO20050118539 A1 | 12/2005 |
| WO | WO20070108936 A2 | 9/2007 |
| WO | WO20080042571 A2 | 4/2008 |
| WO | WO2010118287 A1 | 10/2010 |
| WO | WO2012097744 A1 | 7/2012 |

OTHER PUBLICATIONS

Woerdeman et al., "Therapeutic effects of anabolic androgenic steroids on chronic diseases associated with muscle wasting" Expert Opinion on Investigational Drugs, 20:1, 87-97 (Year: 2011).*
Morley, J. E., "Androgens and aging" Maturitas vol. 38 pp. 61-73 (Year: 2001).*
Allan, et al., *Journal of Steroid Biochemistry & Molecular Biology*, 103:76-83 (2007).
Boros, et al., *Journal of Heterocyclic Chemistry*, 48:733-736 (2011).

* cited by examiner

*Primary Examiner* — Eric Olson
(74) *Attorney, Agent, or Firm* — Wayne J. Dustman

(57) ABSTRACT

This invention relates to non-steroidal compounds that are modulators of androgen receptor, and also to the methods for the making and use of such compounds.

4 Claims, No Drawings

CHEMICAL COMPOUNDS

This application is a continuation of U.S. application Ser. No. 15/358,458 filed on Nov. 22, 2016, which is a continuation of U.S. application Ser. No. 14/549,034 filed on 20 Nov. 2014 (which issued as U.S. Pat. No. 9,533,948 on 3 Jan. 2017), which is a continuation of U.S. application Ser. No. 13/941,911 filed on 15 Jul. 2013 (which issued as U.S. Pat. No. 8,957,104 on 17 Feb. 2015), which claims priority from 61/748,874, filed on 4 Jan. 2013, which claims priority from 61/672,455 filed on 17 Jul. 2012, which are herein incorporated by reference.

FIELD OF THE INVENTION

This invention relates to non-steroidal compounds that are modulators of the androgen receptor and methods for their use in treatment.

BACKGROUND OF THE INVENTION

Steroidal nuclear receptor (NR) ligands are known to play important roles in the health of both men and women. Testosterone (T) and dihydrotestosterone (DHT) are endogenous steroidal ligands for the androgen receptor (AR) that appear to play a role in every tissue type found in the mammalian body. During the development of the fetus, androgens play a role in sexual differentiation and development of male sexual organs.

Further sexual development is mediated by androgens during puberty. Androgens play diverse roles in the adult, including stimulation and maintenance of male sexual accessory organs and maintenance of the musculoskeletal system. Cognitive function, sexuality, aggression, and mood are some of the behavioral aspects mediated by androgens. Androgens have a physiologic effect on the skin, bone, and skeletal muscle, as well as blood, lipids, and blood cells (Chang, C. and Whipple, G. *Androgens and Androgen Receptors*. Kluwer Academic Publishers: Boston, Mass., 2002)

Many clinical studies with testosterone have demonstrated significant gains in muscle mass and function along with decreases in visceral fat. See, for example, Bhasin (2003) S. J. *Gerontol. A Biol. Sci. Med. Sci.* 58:1002-8, and Ferrando, A. A. et al. (2002) *Am. J. Phys. Endo. Met.* 282: E601-E607. Androgen replacement therapy (ART) in men improves body composition parameters such as muscle mass, strength, and bone mineral density (see, for example, Asthana, S. et al. (2004) J. Ger., *Series A: Biol. Sci. Med. Sci.* 59: 461-465). There is also evidence of improvement in less tangible parameters such as libido and mood. Andrologists and other specialists are increasingly using androgens for the treatment of the symptoms of androgen deficiency. ART, using T and its congeners, is available in transdermal, injectable, and oral dosage forms. All current treatment options have contraindications (e.g., prostate cancer) and side-effects, such as increased hematocrit, liver toxicity, and sleep apnoea. Side-effects from androgen therapy in women include: acne, hirsutism, and lowering of high-density lipo-protein (HDL) cholesterol levels, a notable side-effect also seen in men.

Agents that could selectively afford the benefits of androgens and greatly reduce the side-effect profile would be of great therapeutic value. Interestingly, certain NR ligands are known to exert their action in a tissue selective manner (see, for example, Smith et al. (2004) *Endoc. Rev.* 2545-71). This selectivity stems from the particular ability of these ligands to function as agonists in some tissues, while having no effect or even an antagonist effect in other tissues. The term "selective receptor modulator" (SRM) has been given to these molecules. A synthetic compound that binds to an intracellular receptor and mimics the effects of the native hormone is referred to as an agonist. A compound that inhibits the effect of the native hormone is called an antagonist. The term "modulators" refers to compounds that have a spectrum of activities ranging from full agonism to partial agonism to full antagonism.

SARMs (selective androgen receptor modulators) represent an emerging class of small molecule pharmacotherapeutics that have the potential to afford the important benefits of androgen therapy without the undesired side-effects. Many SARMs with demonstrated tissue-selective effects are currently in the early stages of development See, for example, Mohler, M. L. et al. (2009) *J. Med. Chem.* 52(12): 3597-617. One notable SARM molecule, Ostarine™, has recently completed phase I and II clinical studies. See, for example, Zilbermint, M. F. and Dobs, A. S. (2009) *Future Oncology* 5(8):1211-20. Ostarine™ appears to increase total lean body mass and enhance functional performance. Because of their highly-selective anabolic properties and demonstrated androgenic-sparing activities, SARMs should be useful for the prevention and/or treatment of many diseases in both men and women, including, but not limited to sarcopenia, cachexias (including those associated with cancer, heart failure, chronic obstructive pulmonary disease (COPD), and end stage renal disease (ESRD), urinary incontinence, osteoporosis, frailty, dry eye and other conditions associated with aging or androgen deficiency. See, for example, Ho et al. (2004) *Curr Opin Obstet Gynecol.* 16:405-9; Albaaj et al. (2006) *Postgrad Med J* 82:693-6; Caminti et al. (2009) *J Am Coll Cardiol.* 54(10):919-27; Iellamo et al. (2010) *J Am Coll Cardiol.* 56(16):1310-6; Svartberg (2010) *Curr Opin Endocrinol Diabetes Obes.* 17(3):257-61, and Mammadov et al. (2011) *Int Urol Nephrol* 43:1003-8. SARMS also show promise for use in promoting muscle regeneration and repair (see, for example, Serra et al. (Epub 2012 Apr. 12) doi:10.1093/Gerona/gls083), in the areas of hormonal male contraception and benign prostatic hyperplasia (BPH), and in wound healing (see, for example, Demling (2009) *ePlasty* 9:e9).

Preclinical studies and emerging clinical data demonstrate the therapeutic potential of SARMs to address the unmet medical needs of many patients. The demonstrated advantages of this class of compounds in comparison with steroidal androgens (e.g., tissue-selective activity, oral administration, AR selectivity, and lack of androgenic effect) position SARMs for a bright future of therapeutic applications. Accordingly, there remains a need in the art for new SARMs for therapeutic use.

BRIEF SUMMARY OF INVENTION

The present invention relates to non-steroidal compounds that are modulators of androgen receptor, and also to the use of these compounds in therapy.

Briefly, in one aspect, the present invention provides compounds of formula (I):

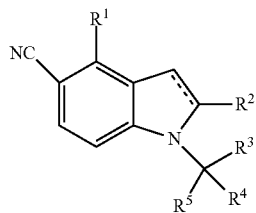

or a salt thereof wherein:

⇜ indicates a single or double bond;
$R^1$ is —$CF_3$, —C≡N, or halo;
$R^2$ is H, $C_{1-3}$ alkyl, or —$CHF_2$;
$R^3$ is H or $C_{1-3}$ alkyl;
$R^4$ is —C(O)O$CH_3$, —C($CH_3$)$_2$OH, —$CH_2$OH, —$CH_2$S$CH_3$, —$CH_2$S(O)$_2$$CH_3$, —C(O)$CH_3$, or phenyl or pyridinyl, wherein said phenyl or pyridinyl is optionally substituted with one or two groups selected from —C≡N and halo; and
$R^5$ is H or methyl.

In another aspect of the invention, ⇜ $R^1$, $R^2$, $R^3$, and $R^5$ are as defined above and $R^4$ is —C(O)O$CH_3$, —C($CH_3$)$_2$OH, —C($CH_3$)($CF_3$)OH, —$CH_2$OH, —$CH_2$S$CH_3$, —$CH_2$S(O)$_2$$CH_3$, —C(O)$CH_3$, or phenyl or pyridinyl, wherein said phenyl or pyridinyl is optionally substituted with one or two groups selected from —C≡N and halo.

In a particular embodiment of the invention, ⇜ indicates a single or double bond; $R^1$ is —$CF_3$, —C≡N, or halo; $R^2$ is H, $C_{1-3}$ alkyl, or —$CHF_2$; $R^3$ is H; $R^4$ is —C($CH_3$)($CF_3$)OH, —$CH_2$S$CH_3$, —$CH_2$S(O)$_2$$CH_3$, —C(O)$CH_3$ or phenyl or pyridinyl, wherein said phenyl or pyridinyl is optionally substituted with one or two groups selected from —C≡N and halo, and $R^5$ is methyl.

In an alternate embodiment of the invention, ⇜ indicates a single or double bond; $R^1$ is —$CF_3$, —C≡N, or halo; $R^2$ is H, $C_{1-3}$ alkyl, or —$CHF_2$; $R^3$ is $C_{1-3}$ alkyl; $R^4$ is —C($CH_3$)($CF_3$)OH, —$CH_2$S$CH_3$, —$CH_2$S(O)$_2$$CH_3$, —C(O)$CH_3$ or phenyl or pyridinyl, wherein said phenyl or pyridinyl is optionally substituted with one or two groups selected from —C≡N and halo, and $R^5$ is H or methyl.

Another aspect of the present invention provides a pharmaceutical composition comprising a compound of the present invention and one or more pharmaceutically acceptable excipients.

Another aspect of the present invention provides a compound of the present invention for use as an active therapeutic substance.

Another aspect of the present invention provides a compound of the present invention for use in the acceleration of wound healing and burn healing, and in the treatment of hypogonadism, sarcopenia, osteoporosis, muscle wasting, wasting diseases, cachexia (including cachexias associated with cancer, chronic obstructive pulmonary disease (COPD), end stage renal disease (ESRD), heart failure, HIV illness, HIV treatment, and diabetes mellitus type 1 and type 2), frailty, dry eye, prostatic hyperplasia, prostate cancer, breast cancer, menopausal and andropausal vasomotor conditions, sexual dysfunction, erectile dysfunction, depression, uterine fibroid disease, endometriosis, urinary incontinence (including urinary incontinence associated with muscle and/or tissue wasting of the pelvic floor), acne, hirsutism, male contraception, impotence, and in the use as male and female hormone replacement therapy, as a stimulant of hematopoiesis, and as an anabolic agent.

Another aspect of the present invention provides the use of a compound of the present invention in the manufacture of a medicament for use in the acceleration of wound healing and the treatment of hypogonadism, sarcopenia, osteoporosis, muscle wasting, wasting diseases, muscle wasting and cachexia (including muscle wasting and cachexias associated with cancer, chronic obstructive pulmonary disease (COPD), end stage renal disease (ESRD), heart failure, HIV illness, HIV treatment, and diabetes mellitus type 1 and type 2), frailty, dry eye, prostatic hyperplasia, prostate cancer, breast cancer, menopausal and andropausal vasomotor conditions, urinary incontinence (including urinary incontinence associated with muscle and/or tissue wasting of the pelvic floor), sexual dysfunction, erectile dysfunction, depression, uterine fibroid disease, endometriosis, acne, hirsutism, male contraception, impotence, and in the use as male and female hormone replacement therapy, as a stimulant of hematopoiesis, and as an anabolic agent.

Another aspect of the present invention provides a method for the treatment of hypogonadism, sarcopenia, osteoporosis, muscle wasting, wasting diseases, cachexia and muscle wasting (including muscle wasting and cachexias associated with cancer, chronic obstructive pulmonary disease (COPD), end stage renal disease (ESRD), heart failure, HIV illness, HIV treatment, and diabetes mellitus type 1 and type 2), frailty, prostatic hyperplasia, prostate cancer, breast cancer, menopausal and andropausal vasomotor conditions, chronic obstructive pulmonary disease (COPD), urinary incontinence (including urinary incontinence associated with muscle and/or tissue wasting of the pelvic floor), sexual dysfunction, erectile dysfunction, depression, uterine fibroid disease, endometriosis, acne, hirsutism, male contraception, impotence, and a method of male and female hormone replacement therapy, stimulation of hematopoiesis, and anabolism, comprising the administration of a compound of the present invention.

In another aspect, the present invention provides a method for the treatment of a muscle injury, and for accelerating muscle repair comprising the administration of a compound of the present invention. Also provided is the use of a compound of the present invention in the treatment of a muscle injury, or in the acceleration of muscle repair. Additionally included is the use of a compound of the present invention in the manufacture of a medicament for the treatment of muscle injury or the acceleration of muscle repair.

DETAILED DESCRIPTION OF THE INVENTION

In one aspect, the present invention provides compounds of formula (I):

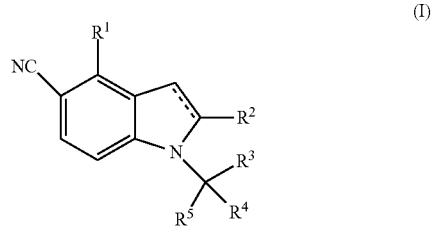

or a salt thereof wherein:

⎸ indicates a single or double bond;
$R^1$ is —$CF_3$, —C≡N, or halo;
$R^2$ is H, $C_{1-3}$ alkyl, or —$CHF_2$;
$R^3$ is H or $C_{1-3}$ alkyl;
$R^4$ is —$C(O)OCH_3$, —$C(CH_3)_2OH$, —$CH_2OH$, —$CH_2SCH_3$, —$CH_2S(O)_2CH_3$, —$C(O)CH_3$, or phenyl or pyridinyl, wherein said phenyl or pyridinyl is optionally substituted with one or two groups selected from —C≡N and halo; and
$R^5$ is H or methyl.

In another aspect of the invention, ⎸ $R^1$, $R^2$, $R^3$, and $R^5$ are as defined above and $R^4$ is —$C(O)OCH_3$, —$C(CH_3)_2OH$, —$C(CH_3)(CF_3)OH$, —$CH_2OH$, —$CH_2SCH_3$, —$CH_2S(O)_2CH_3$, —$C(O)CH_3$, or phenyl or pyridinyl, wherein said phenyl or pyridinyl is optionally substituted with one or two groups selected from —C≡N and halo.

In one embodiment, ⎸ indicates a single or double bond; $R^1$ is —$CF_3$, —C≡N, or halo; $R^2$ is H, $C_{1-3}$ alkyl, or —$CHF_2$; $R^3$ is H or $C_{1-3}$ alkyl;
$R^4$ is, —$CH_2S(O)_2CH_3$, and $R^5$ is H or methyl.

In a particular embodiment of the invention, ⎸ indicates a single or double bond; $R^1$ is —$CF_3$, —C≡N, or halo; $R^2$ is H, $C_{1-3}$ alkyl, or —$CHF_2$; $R^3$ is H;
$R^4$ is —$C(CH_3)(CF_3)OH$, —$CH_2SCH_3$, —$CH_2S(O)_2CH_3$, —$C(O)CH_3$ or phenyl or pyridinyl, wherein said phenyl or pyridinyl is optionally substituted with one or two groups selected from —C≡N and halo, and $R^5$ is methyl.

In an alternate embodiment of the invention, ⎸ indicates a single or double bond; $R^1$ is —$CF_3$, —C≡N, or halo; $R^2$ is H, $C_{1-3}$ alkyl, or —$CHF_2$; $R^3$ is $C_{1-3}$ alkyl; $R^4$ is —$C(CH_3)(CF_3)OH$, —$CH_2SCH_3$, —$CH_2S(O)_2CH_3$, —$C(O)CH_3$ or phenyl or pyridinyl, wherein said phenyl or pyridinyl is optionally substituted with one or two groups selected from —C≡N and halo, and $R^5$ is H or methyl.

In some embodiments, $R^1$ is —$CF_3$, —C≡N, or halo. In certain embodiments, $R^1$ is —$CF_3$ or —C≡N. In certain embodiments, $R^1$ is halo. In particular embodiments, $R^1$ is Cl. In some preferred embodiments, $R^1$ is —$CF_3$.

In some embodiments, $R^2$ is H, methyl, ethyl, propyl, or —$CHF_2$. In particular embodiments, $R^2$ is H, methyl, or —$CHF_2$. In certain preferred embodiments, $R^2$ is H. In other preferred embodiments, $R^2$ is methyl.

In certain embodiments, $R^3$ is H. In other embodiments, $R^3$ is $C_{1-3}$alkyl. In particular embodiments, $R^3$ is methyl or ethyl. In certain preferred embodiments, $R^3$ is methyl.

In some embodiments, $R^4$ is —$C(O)OCH_3$, —$C(CH_3)_2OH$, —$CH_2OH$, —$CH_2SCH_3$, —$CH_2S(O)_2CH_3$, or —$C(O)CH_3$. In other embodiments, $R^4$ is —$C(CH_3)(CF_3)OH$. In preferred embodiments $R^4$ is —$C(CH_3)_2OH$ or —$CH_2S(O)_2CH_3$. In particularly preferred embodiments, $R^4$ is —$CH_2S(O)_2CH_3$.

In other embodiments, $R^4$ is phenyl or pyridinyl, wherein said phenyl or pyridinyl is optionally substituted with one or two groups selected from —C≡N and halo. In certain embodiments, $R^4$ is:

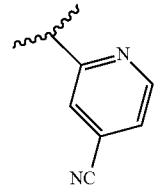 [SMILES: *c1cc(C#N)ccn1]

In one embodiment, $R^5$ is H. In another embodiment, $R^5$ is methyl.

In some embodiments, $R^3$ is H; $R^4$ is —$C(CH_3)_2OH$, —$CH_2SCH_3$, or phenyl or pyridinyl, wherein said phenyl or pyridinyl is optionally substituted with one or two groups selected from —C≡N and halo, and $R^5$ is H.

In alternate embodiments, $R^3$ is methyl, ethyl, or propyl, $R^4$ is —$C(O)OCH_3$, —$C(CH_3)_2OH$, —$CH_2OH$, —$CH_2SCH_3$, —$CH_2S(O)_2CH_3$, —$C(O)CH_3$, or phenyl or pyridinyl, wherein said phenyl or pyridinyl is optionally substituted with one or two groups selected from —C≡N and halo, and $R^5$ is H.

In an additional embodiment, $R^3$ is methyl, ethyl, or propyl; $R^4$ is —$C(CH_3)_2OH$; and $R^5$ is H.

In an another embodiment, $R^3$ is methyl, ethyl, or propyl; $R^4$ is —$C(CH_3)$ ($CF5_3$)OH; and $R^5$ is H.

In one preferred embodiment, the compound is a compound of Formula I':

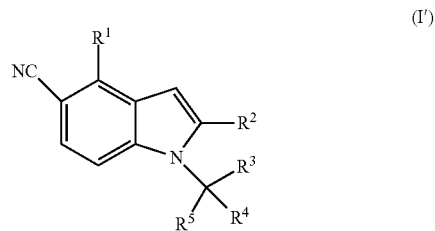

(I')

where $R^1$, $R^2$, $R^3$, $R^4$, and $R^5$, are as defined above.

In an alternate embodiment, the compound is a compound of Formula I":

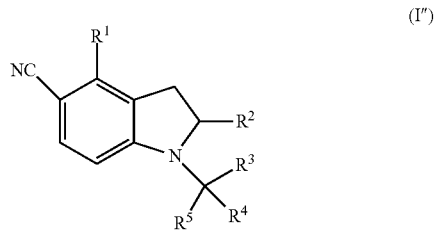

(I")

where $R^1$, $R^2$, $R^3$, $R^4$, and $R^5$, are as defined above.

As used herein the term "halo" or "halogen" refers to fluoro, chloro, bromo, or iodo groups.

As used herein the term "alkyl" refers to a straight or branched chain hydrocarbon, preferably having the specified number of carbon atoms. Examples of "alkyl" as used herein include, but are not limited to, methyl, ethyl, propyl, iso-propyl.

As used throughout this specification, the preferred number of atoms, such as carbon atoms, will be represented by, for example, the phrase "Cx-Cy alkyl," which refers to an alkyl group, as herein defined, containing the specified number of carbon atoms.

While the embodiments and preferred groups for each variable have generally been listed above separately for each variable, compounds of this invention include those in which several of each variable in formula (I), (I'), or (I") are selected from the aspects or embodiments, and preferred, more preferred, or most preferred groups for each variable. Therefore, this invention is intended to include all combinations of all aspects, embodiments, and preferred, more preferred, and most preferred groups.

The invention also provides compounds selected from the list consisting of:

Methyl 2-[5-cyano-2-methyl-4-(trifluoromethyl)-1H-indol-1-yl]propanoate;
Methyl 2-[5-cyano-2-methyl-4-(trifluoromethyl)-1H-indol-1-yl]butanoate;
2-Methyl-1-(1-methyl-2-oxopropyl)-4-(trifluoromethyl)-1H-indole-5-carbonitrile;
1-(2-Hydroxy-1,2-di methyl propyl)-2-methyl-4-(trifluoromethyl)-1H-indole-5-carbonitrile;
1-(1-Ethyl-2-oxopropyl)-2-methyl-4-(trifluoromethyl)-1H-indole-5-carbonitrile;
1-(1-Ethyl-2-hydroxy-2-methylpropyl)-2-methyl-4-(trifluoromethyl)-1H-indole-5-carbonitrile;
1-(1-Hydroxypropan-2-yl)-2-methyl-4-(trifluoromethyl)-1H-indole-5-carbonitrile;
2-Methyl-1-(1-(methylthio)propan-2-yl)-4-(trifluoromethyl)-1H-indole-5-carbonitrile;
2-Methyl-1-(1-(methylsulfonyl)propan-2-yl)-4-(trifluoromethyl)-1H-indole-5-carbonitrile;
2-Methyl-1-(1-(methylthio)butan-2-yl)-4-(trifluoromethyl)-1H-indole-5-carbonitrile;
2-Methyl-1-(1-(methylsulfonyl)butan-2-yl)-4-(trifluoromethyl)-1H-indole-5-carbonitrile;
1-(2-Hydroxy-2-methylpropyl)-2-propyl-4-(trifluoromethyl)-1H-indole-5-carbonitrile;
1-(3-Hydroxy-3-methylbutan-2-yl)-2-propyl-4-(trifluoromethyl)-1H-indole-5-carbonitrile;
1-(2-(Methylthio)ethyl)-2-propyl-4-(trifluoromethyl)-1H-indole-5-carbonitrile;
1-(1-(Methylthio)propan-2-yl)-2-propyl-4-(trifluoromethyl)-1H-indole-5-carbonitrile;
2-(Difluoromethyl)-1-(3-hydroxy-3-methylbutan-2-yl)-1H-indole-4,5-dicarbonitrile;
2-(Difluoromethyl)-1-(1-(methylthio)propan-2-yl)-1H-indole-4,5-dicarbonitrile;
2-(Difluoromethyl)-1-(1-(methylsulfonyl)propan-2-yl)-1H-indole-4,5-dicarbonitrile;
1-(3-Oxobutan-2-yl)-4-(trifluoromethyl)-1H-indole-5-carbonitrile;
1-(3-Hydroxy-3-methylbutan-2-yl)-4-(trifluoromethyl)-1H-indole-5-carbonitrile;
(S)-1-(3-Hydroxy-3-methylbutan-2-yl)-4-(trifluoromethyl)-1H-indole-5-carbonitrile;
(R)-1-(3-Hydroxy-3-methylbutan-2-yl)-4-(trifluoromethyl)-1H-indole-5-carbonitrile;
(R)-1-(3-Hydroxy-3-methylbutan-2-yl)-4-(trifluoromethyl) indoline-5-carbonitrile;
1-(2-Hydroxy-2-methylpentan-3-yl)-4-(trifluoromethyl)-1H-indole-5-carbonitrile;
1-(1-(Methylthio)propan-2-yl)-4-(trifluoromethyl)-1H-indole-5-carbonitrile;
1-(1-(Methylsulfonyl)propan-2-yl)-4-(trifluoromethyl)-1H-indole-5-carbonitrile;
(R)-1-(1-(Methylsulfonyl)propan-2-yl)-4-(trifluoromethyl)-1H-indole-5-carbonitrile;
(R)-1-(1-(Methylsulfonyl)propan-2-yl)-4-(trifluoromethyl) indoline-5-carbonitrile;
1-(1-(Methylthio)butan-2-yl)-4-(trifluoromethyl)-1H-indole-5-carbonitrile;
1-(1-(Methylsulfonyl)butan-2-yl)-4-(trifluoromethyl)-1H-indole-5-carbonitrile;
4-Chloro-1-(3-oxobutan-2-yl)-1H-indole-5-carbonitrile;
(S)-4-Chloro-1-(3-hydroxy-3-methylbutan-2-yl)-1H-indole-5-carbonitrile;
(R)-4-Chloro-1-(3-hydroxy-3-methylbutan-2-yl)-1H-indole-5-carbonitrile;
4-Chloro-1-(2-hydroxy-2-methylpentan-3-yl)-1H-indole-5-carbonitrile;
4-Chloro-1-(3-hydroxy-2,3-dimethylbutan-2-yl)-1H-indole-5-carbonitrile;
(S)-4-Chloro-1-(1-(methylthio)propan-2-yl)-1H-indole-5-carbonitrile;
(S)-4-Chloro-1-(1-(methylsulfonyl)propan-2-yl)-1H-indole-5-carbonitrile;
(R)-4-Chloro-1-(1-(methylthio)propan-2-yl)-1H-indole-5-carbonitrile;
(R)-4-Chloro-1-(1-(methylsulfonyl)propan-2-yl)-1H-indole-5-carbonitrile;
(S)-1-(3-Hydroxy-3-methylbutan-2-yl)-1H-indole-4,5-dicarbonitrile; (R)-1-(3-Hydroxy-3-methylbutan-2-yl)-1H-indole-4,5-dicarbonitrile;
1-(2-Hydroxy-2-methylpentan-3-yl)-1H-indole-4,5-dicarbonitrile;
1-(3-Hydroxy-2,3-dimethylbutan-2-yl)-1H-indole-4,5-dicarbonitrile;
(R)-1-(1-(Methylsulfonyl)propan-2-yl)-1H-indole-4,5-dicarbonitrile;
(R)-1-(1-(3-Cyanophenyl)ethyl)-4-(trifluoromethyl)-1H-indole-5-carbonitrile;
1-(1-(3-Cyanophenyl)propyl)-4-(trifluoromethyl)-1H-indole-5-carbonitrile;
(R)-1-(1-(5-Cyanopyridin-3-yl)propyl)-4-(trifluoromethyl)-1H-indole-5-carbonitrile;
(R)-4-Chloro-1-(1-(5-cyanopyridin-3-yl)propyl)-1H-indole-5-carbonitrile;
(R)-1-(1-Phenylethyl)-1H-indole-4,5-dicarbonitrile;
(R)-1-(1-(3-Cyanophenyl)ethyl)-1H-indole-4,5-dicarbonitrile;
(R)-1-(1-(5-Cyanopyridin-3-yl)propyl)-1H-indole-4,5-dicarbonitrile;
and salts thereof.

The invention also encompasses the compound 4-Chloro-1-((2R,3S)-4,4,4-trifluoro-3-hydroxy-3-methylbutan-2-yl)-1H-indole-5-carbonitrile and salts thereof.

The invention also provides compounds selected from the list consisting of:

1-((2R,3S)-4,4,4-trifluoro-3-hydroxy-3-methyl butan-2-yl)-4-(trifluoromethyl)-1H-indole-5-carbonitrile;
(S)-1-(1-(Methylthio)propan-2-yl)-4-(trifluoromethyl)-1H-indole-5-carbonitrile;
(S)-1-(1-(Methylsulfonyl)propan-2-yl)-4-(trifluoromethyl)-1H-indole-5-carbonitrile;
and salts thereof.

In a preferred embodiment, the compound is (R)-1-(1-(methylsulfonyl)propan-2-yl)-4-(trifluoromethyl)-1H-indole-5-carbonitrile.

The compounds of the present invention are believed to modulate the function of one or more nuclear hormone receptor(s). Particularly, the compounds of the present invention modulate the androgen receptor ("AR"). The present invention includes compounds that are selective agonists, partial agonists, antagonists, or partial antagonists of the AR. Compounds of the present invention are useful in the treatment of AR-associated diseases and conditions, for example, a disease or condition that is prevented, alleviated, or cured through the modulation of the function or activity of AR. Such modulation may be isolated within certain tissues or widespread throughout the body of the subject being treated.

As used herein, the term "treatment" refers to alleviating the specified condition, eliminating or reducing the symptoms of the condition, slowing or eliminating the progression of the condition.

The compounds of the present may invention may also be useful in preventing or delaying the initial occurrence of the condition in a subject, or reoccurrence of the condition in a previously afflicted subject.

One embodiment of the present invention provides compounds of the present invention for use in medical therapy. Particularly, the present invention provides for the treatment of disorders mediated by androgenic activity. More particularly, the present invention provides treatment of disorders responsive to tissue-selective anabolic and or androgenic activity. A further embodiment of the invention provides a method of treatment of a mammal suffering from a disorder mediated by androgenic activity, which includes administering to said subject an effective amount of a compound of the present invention.

One embodiment of the present invention is the use of the compounds of the present invention for the treatment of a variety of disorders including, but not limited to, osteoporosis and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline (ARFD), dry eye, sarcopenia, end-stage renal disease (ESRD), chronic fatigue syndrome, chronic myalgia, acute fatigue syndrome, sepsis, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, menopausal vasomotor conditions, urinary incontinence, atherosclerosis, libido enhancement, sexual dysfunction, depression, nervousness, irritability, stress, reduced mental energy and low self-esteem, improvement of cognitive function, endometriosis, polycystic ovary syndrome, counteracting preeclampsia, premenstrual syndrome, contraception, uterine fibroid disease, aortic smooth muscle cell proliferation, male hormone replacement, or ADAM.

A further embodiment of the invention provides a method of treatment of a mammal requiring the treatment of a variety of disorders including, but not limited to, osteoporosis and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline (ARFD), dry eye, sarcopenia, end-stage renal disease (ESRD), chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, menopausal vasomotor conditions, urinary incontinence (including urinary incontinence associated with muscle and/or tissue wasting of the pelvic floor), atherosclerosis, libido enhancement, sexual dysfunction, depression, nervousness, irritability, stress, reduced mental energy and low self-esteem, improvement of cognitive function, endometriosis, polycystic ovary syndrome, counteracting preeclampsia, premenstrual syndrome, contraception, uterine fibroid disease, aortic smooth muscle cell proliferation, male hormone replacement, or ADAM. Preferably the compounds of the present invention are used as male and female hormone replacement therapy or for the treatment or prevention of hypogonadism, osteoporosis, muscle wasting, wasting diseases, cancer cachexia, frailty, prostatic hyperplasia, prostate cancer, breast cancer, menopausal and andropausal vasomotor conditions, urinary incontinence, sexual dysfunction, erectile dysfunction, depression, uterine fibroid disease, and/or endometriosis, treatment of acne, hirsutism, stimulation of hematopoiesis, male contraception, impotence, and as anabolic agents, which use includes administering to a subject an effective amount of a compound of the present invention.

In some embodiments, the invention encompasses the use of a compound of the invention in the treatment of muscle injury. In particular embodiments, the muscle injury is a surgery-related muscle injury, a traumatic muscle injury, a work-related skeletal muscle injury, or an overtraining-related muscle injury.

Non-limiting examples of surgery-related muscle injuries include muscle damage due to knee replacement, anterior cruciate ligament (ACL) repair, plastic surgery, hip replacement surgery, joint replacement surgery, tendon repair surgery, surgical repair of rotator cuff disease and injury, and amputation.

Non-limiting examples of traumatic muscle injuries include battlefield muscle injuries, auto accident-related muscle injuries, and sports-related muscle injuries. Traumatic injury to the muscle can include lacerations, blunt force contusions, shrapnel wounds, muscle pulls or tears, burns, acute strains, chronic strains, weight or force stress injuries, repetitive stress injuries, avulsion muscle injury, and compartment syndrome.

In one embodiment, the muscle injury is a traumatic muscle injury and the treatment method provides for administration of at least one high dose of a compound of the invention immediately after the traumatic injury (for example, within one day of the injury) followed by periodic administration of a low dose of a compound of the invention during the recovery period.

Non-limiting examples of work-related muscle injuries include injuries caused by highly repetitive motions, forceful motions, awkward postures, prolonged and forceful mechanical coupling between the body and an object, and vibration.

Overtraining-related muscle injuries include unrepaired or under-repaired muscle damage coincident with a lack of recovery or lack of an increase of physical work capacity.

In an additional embodiment, the muscle injury is exercise or sports-induced muscle damage resulting including exercise-induced delayed onset muscle soreness (DOMS).

In another aspect, the invention provides a method of treating a muscle degenerative disorder comprising administering to a human a compound of the invention.

In particular embodiments, the muscle degenerative disorder is muscular dystrophy, myotonic dystrophy, polymyositis, or dermatomyositis.

For example, the methods may be used to treat a muscular dystrophy disorder selected from Duchenne MD, Becker MD, Congenital MD (Fukuyama), Emery Dreifuss MD, Limb girdle MD, and Fascioscapulohumeral MD.

The methods of the invention may also be used to treat myotonic dystrophy type I (DM1 or Steinert's), myotonic dystrophy type II (DM2 or proximal myotonic myopathy), or congenital myotonia.

In some embodiments, the invention encompasses a therapeutic combination in which the compound of the invention is administered in a subject in combination with the implantation of a biologic scaffold (e.g. a scaffold comprising extracellular matrix) that promotes muscle regeneration. Such scaffolds are known in the art. See, for example, Turner and Badylack (2012) Cell Tissue Res. 347(3):759-74 and U.S. Pat. No. 6,576,265. Scaffolds comprising non-cross-linked extracellular matrix material are preferred.

In another aspect, the invention provides a method of treating tendon damage where the method comprises administering a compound of the invention to a subject in need thereof. In a particular embodiment, the invention includes a method of enhancing the formation of a stable tendon-bone interface. In a related embodiment, the invention provides a method of increasing the stress to failure of tendons, for example surgically-repaired tendons. In an additional embodiment, the invention provides a method of reducing fibrosis at the repair site for surgically-repaired tendons. In a particular embodiment, the invention provides a method of treating tendon damage associated with rotator cuff injury, or tendon damage associated with surgical repair of rotator cuff injury. The mammal requiring treatment with a compound of the present invention is typically a human being.

In one preferred embodiment, the disorder to be treated is muscle wasting associated with chronic obstructive pulmonary disease (COPD).

In another preferred embodiment, the disorder to be treated is muscle wasting associated with chronic kidney disease (CKD) or end stage renal disease (ESRD).

In an alternate preferred embodiment, the disorder to be treated is muscle wasting associated with chronic heart failure (CHF).

In an additional preferred embodiment, the compound is used to accelerate bone fracture repair and healing, for example to accelerate the repair and healing of a hip fracture.

In yet another preferred embodiment, the compound is used to treat urinary incontinence (including urinary incontinence associated with muscle and/or tissue wasting of the pelvic floor).

The compounds of the present invention may crystallize in more than one form, a characteristic known as polymorphism, and such polymorphic forms ("polymorphs") are within the scope of formula (I), (I'), or (I"). Polymorphism generally may occur as a response to changes in temperature, pressure, or both. Polymorphism may also result from variations in the crystallization process. Polymorphs may be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by formula (I), (I'), or (I"), as well as any wholly or partially equilibrated mixtures thereof. The present invention also includes the individual isomers of the compounds represented by the formulas above as mixtures with isomers thereof in which one or more chiral centers are inverted.

Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. Representative salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

As used herein, the term "solvate" refers to a complex of variable stoichiometry formed by a solute (in this invention, a compound of formula (I), (I'), or (I")) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "effective amount" means that amount of a drug or pharmaceutical agent that will elicit the biological or medical response of a tissue, system, animal, or human that is being sought, for instance, by a researcher or clinician. The biological or medical response may be considered a prophylactic response or a treatment response. The term "therapeutically effective amount" means any amount which, as compared to a corresponding subject who has not received such amount, results in improved treatment, healing or amelioration of a disease, disorder, or side effect, or a decrease in the rate of advancement of a disease or disorder. The term also includes within its scope amounts effective to enhance normal physiological function. For use in therapy, therapeutically effective amounts of a compound of formula (I) (I'), or (I") may be administered as the raw chemical. Additionally, the active ingredient may be presented as a pharmaceutical composition.

Accordingly, the invention further provides pharmaceutical compositions that include effective amounts of compounds of the present invention and one or more pharmaceutically acceptable carriers, diluents, or excipients. The compounds of the present invention are as herein described. The carrier(s), diluent(s) or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a compound of the present invention with one or more pharmaceutically acceptable carriers, diluents or excipients.

A therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. An effective amount of a compound of the present invention for the treatment of humans suffering from disorders such as frailty, generally, should be in the range of 0.01 to 100 mg/kg body weight of recipient (mammal) per day. More usually the effective amount should be in the range of 0.001 to 1 mg/kg body weight per day. Thus, for a 70 kg adult mammal the actual amount per day would usually be from 0.07 to 70 mg, such as 0.1-20 mg, for example 1-10 mg. This amount may be given in a single dose per day or in a number (such as two, three, four, five, or more) of sub-doses per day such that the total daily dose is the same. An effective amount of a salt, solvate may be determined as a proportion of the effective amount of the compound of formula (I), (I'), or (I") per se. Similar dosages should be appropriate for treatment of the other conditions referred to herein.

Pharmaceutical formulations may be presented in unit dose forms containing a predetermined amount of active ingredient per unit dose. Such a unit may contain, as a non-limiting example, 0.1 mg to 100 mg of a compound of the present invention, such as 0.1-50 mg, for example 0.5-15 mg depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component may be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents may also be present.

Capsules can be made by preparing a powder, liquid, or suspension mixture and encapsulating with gelatin or some other appropriate shell material. Glidants and lubricants such as colloidal silica, talc, magnesium stearate, calcium stearate, or solid polyethylene glycol may be added to the mixture before the encapsulation. A disintegrating or solubilizing agent such as agar-agar, calcium carbonate or sodium carbonate may also be added to improve the availability of the medicament when the capsule is ingested. Moreover, when desired or necessary, suitable binders, lubricants, disintegrating agents, and coloring agents may also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets can be formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture may be wet-granulated with a binder such as syrup, starch paste, acadia mucilage or solutions of cellulosic or polymeric materials, and forcing through a screen. As an alternative to granulating, the powder mixture may be run through the tablet machine and the result is imperfectly formed slugs broken into granules. The granules may be lubricated to prevent sticking to the tablet forming dies by means of the addition of stearic acid, a stearate salt, talc or mineral oil. The lubricated mixture is then compressed into tablets. The compounds of the present invention may also be combined with a free flowing inert carrier and compressed into tablets directly without going through the granulating or slugging steps. A clear or opaque protective coating consisting of a sealing coat of shellac, a coating of sugar or polymeric material, and a polish coating of wax may be provided. Dyestuffs may be added to these coatings to distinguish different unit dosages.

Oral fluids such as solutions, syrups, and elixirs may be prepared in dosage unit form so that a given quantity contains a predetermined amount of the compound. Syrups may be prepared, for example, by dissolving the compound in a suitably flavored aqueous solution, while elixirs are prepared through the use of a non-toxic alcoholic vehicle. Suspensions may be formulated generally by dispersing the compound in a non-toxic vehicle. Solubilizers and emulsifiers such as ethoxylated isostearyl alcohols and polyoxy ethylene sorbitol ethers may be added. Solubilizers that may be used according to the present invention include Cremophor EL, vitamin E, PEG, and Solutol. Preservatives and/or flavor additives such as peppermint oil, or natural sweeteners, saccharin, or other artificial sweeteners; and the like may also be added.

Where appropriate, dosage unit formulations for oral administration may be microencapsulated. The formulation may also be prepared to prolong or sustain the release as for example by coating or embedding particulate material in polymers, wax or the like.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

The compounds of the present invention may also be delivered by the use of monoclonal antibodies as individual carriers to which the compound molecules are coupled.

The compounds of the present invention may also be coupled with soluble polymers as targetable drug carriers. Such polymers may include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from a patch by chemical enhancers, iontophoresis, noncavitational ultrasound, microneedles, thermal ablation, microdermabrasion, and electroporation as generally described in *Nature Biotechnology,* 26(11), 1261-1268 (2008), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

The compounds of the present invention and their salts, and solvates thereof, may be employed alone or in combination with other therapeutic agents for the treatment of the above-mentioned conditions. For example, in frailty therapy, combination may be had with other anabolic or osteoporosis therapeutic agents. As one example, osteoporosis combination therapies according to the present invention would thus comprise the administration of at least one compound of the present invention and the use of at least one other osteoporosis therapy such as, for example, Boniva® (ibandronate sodium), Fosamax® (alendronate), Actonel® (risedronate sodium), or Prolia™ (denosumab) The compound(s) of the present invention and the other pharmaceutically active agent(s) may be administered together or separately and, when administered separately, administration may occur simultaneously or sequentially, in any order. The amounts of the compound(s) of the present invention and the other pharmaceutically active agent(s) and the relative timings of administration will be selected in order to achieve the desired combined therapeutic effect. The administration in combination of a compound of the present invention with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

Other potential therapeutic combinations include the compounds of the present invention combined with other compounds of the present invention, growth promoting agents, growth hormone secretagogues (e.g., ghrelin), growth hormone releasing factor and its analogs, human growth hormone and its analogs (e.g., Genotropin®, Humatrope®, Norditropin®, Nutropin®, Saizen®, Serostim®), somatomedins, alpha-adrenergic agonists, serotonin 5-HT$_D$ agonists, agents that inhibit somatostatin or its release, 5-α-reductase inhibitors, aromatase inhibitors, GnRH agonists or antagonists, parathyroid hormone, estrogen, testosterone, SERMs, progesterone receptor agonists or antagonists, and/or with other modulators of nuclear hormone receptors.

The compounds of the present invention may be used in the treatment of a variety of disorders and conditions and, as such, the compounds of the present invention may be used in combination with a variety of other suitable therapeutic agents useful in the treatment of those disorders or conditions. Non-limiting examples include combinations of the present invention with anti-diabetic agents, anti-osteoporosis agents, anti-obesity agents, anti-inflammatory agents, anti-anxiety agents, anti-depressants, anti-hypertensive agents, anti-platelet agents, anti-thrombotic and thrombolytic agents, cardiac glycosides, cholesterol or lipid lowering agents, mineralocorticoid receptor antagonists, phosphodiesterase inhibitors, kinase inhibitors, thyroid mimetics, anabolic agents, viral therapies, cognitive disorder therapies, sleeping disorder therapies, sexual dysfunction therapies, contraceptives, cytotoxic agents, radiation therapy, anti-proliferative agents, and anti-tumor agents. Additionally, the compounds of the present invention may be combined with nutritional supplements such as amino acids, triglycerides, vitamins (including vitamin D; see, for example Hedström et al. (2002) *J Bone Joint Surg Br.* 84(4):497-503), minerals, creatine, piloic acid, carnitine, or coenzyme Q10.

In particular, the compounds of the present invention are believed useful, either alone or in combination with other agents in the acceleration of wound healing and burn healing and the treatment of hypogonadism, sarcopenia, osteoporosis, muscle wasting, wasting diseases, cachexia (including cachexias associated with cancer, chronic obstructive pulmonary disease (COPD), end stage renal disease (ESRD), heart failure, HIV illness, HIV treatment, and diabetes mellitus type 1 and type 2), frailty, dry eye, prostatic hyperplasia, prostate cancer, breast cancer, menopausal and andropausal vasomotor conditions, urinary incontinence, sexual dysfunction, erectile dysfunction, depression, uterine fibroid disease, endometriosis, acne, hirsutism, male contraception, impotence, and in the use as male and female hormone replacement therapy, as a stimulant of hematopoiesis, and as an anabolic agent.

The compounds of this invention may be made by a variety of methods, including well-known standard synthetic methods. Illustrative general synthetic methods are set out below and then specific compounds of the invention are prepared in the working Examples.

In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of formula (I), (I'), or (I").

Those skilled in the art will recognize if a stereocenter exists in compounds of formula (I), (I'), or (I"). Accordingly, the present invention includes all possible stereoisomers and includes not only racemic compounds but the individual enantiomers as well. When a compound is desired as a single enantiomer, such may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994), incorporated by reference with regard to stereochemistry.

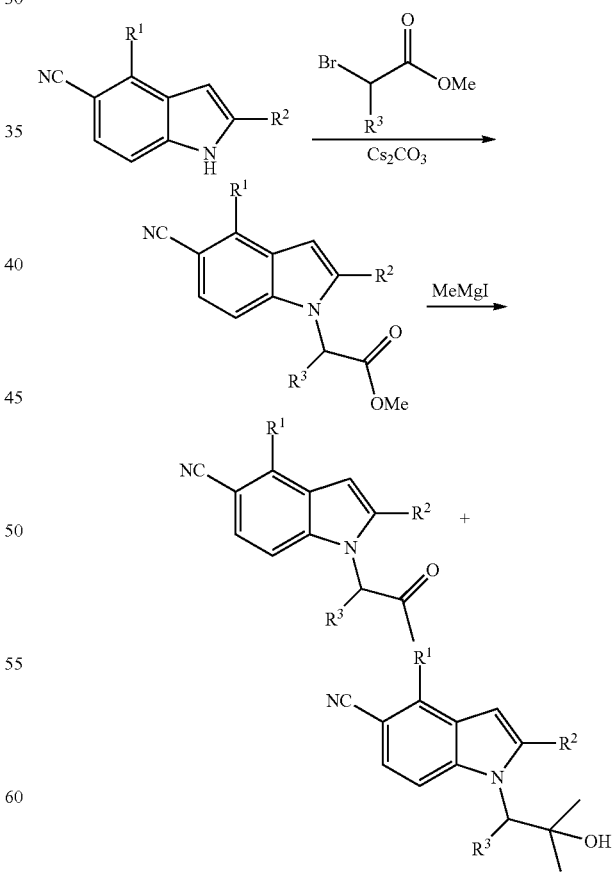

Scheme 1

Compounds of formula (I) can be synthesized by alkylation of highly substituted indoles with alpha haloesters (Scheme 1). The starting indoles can be made according to published procedures (see, for example, US2008139631A1). The respective esters are then subjected to addition of Grignard reagents such as methylmagnesium iodide to afford mixtures of methylketones and tertiary alcohols.

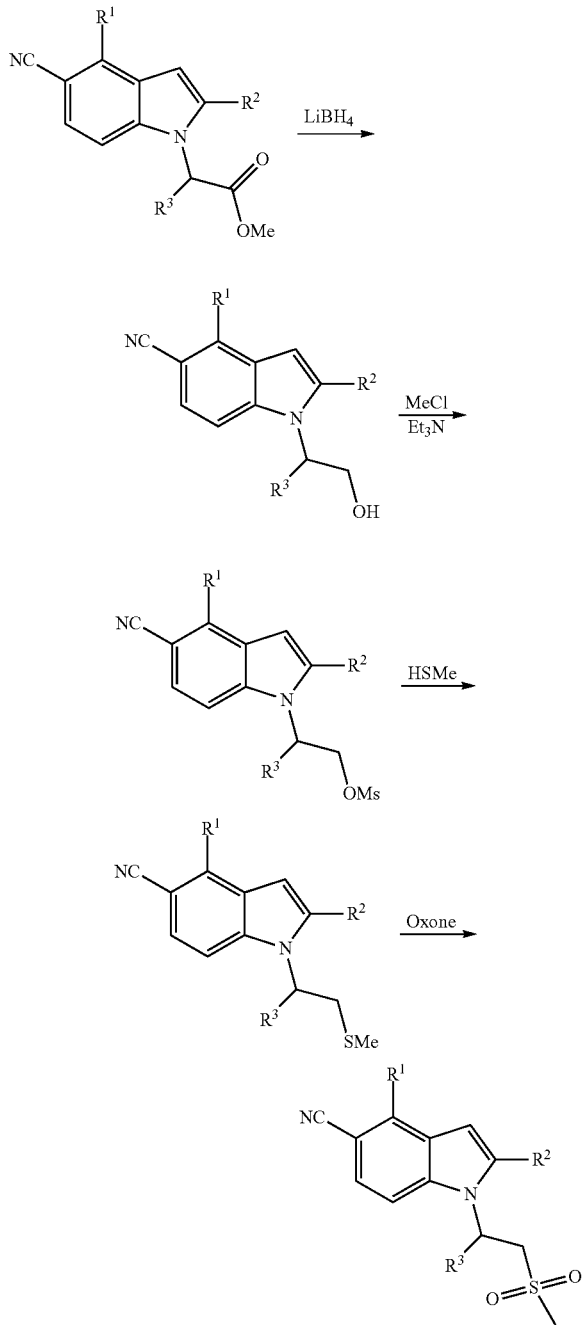

Further structural diversification to afford compounds of formula (I) comes from reduction of the same ester bearing indoles of Scheme 1 (Scheme 2). The resulting primary alcohols are then treated with mesyl chloride followed by sodium thiomethoxide to provide thioethers. Oxidation with Oxone provides the corresponding methyl sulfones.

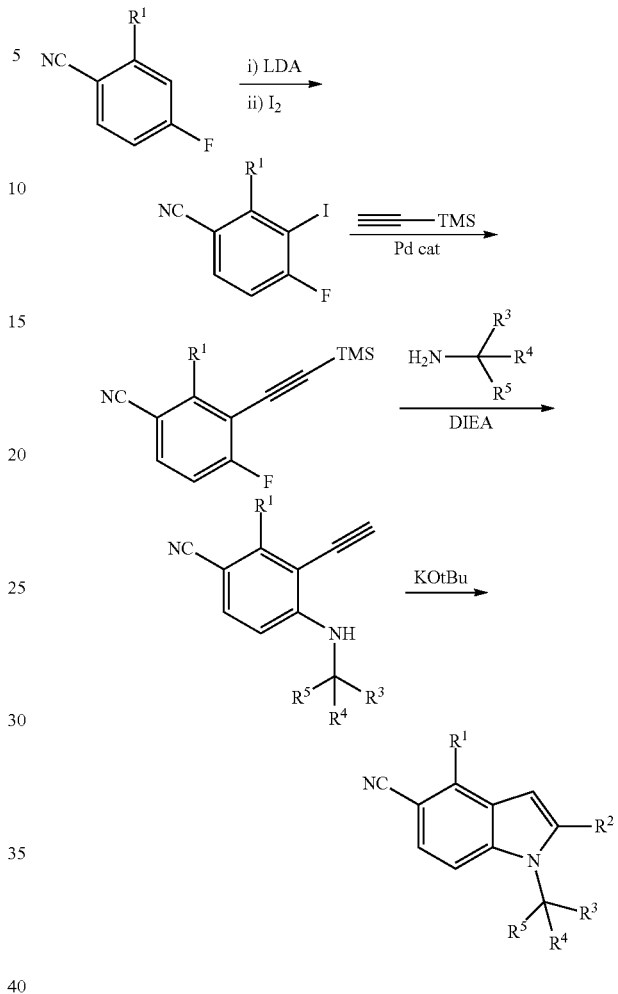

Another method affords compounds of formula (I) stems from highly substituted aryl fluorides made by simple aryl lithiation of commercially available 4-fluorobenzonitriles followed by quenching with iodine (Scheme 3). The corresponding iodoarenes are then coupled to TMS-acetylene through standard palladium mediated synthetic methods. The resulting alkynylarenes are then treated with amines to afford secondary aniline intermediates which cyclize to the corresponding indoles upon treatment with a base. Non-commercially available amine partners for the nucleophilic substitution step are synthesized by standard methods.

ABBREVIATIONS

As used herein the symbols and conventions used in these processes, schemes and examples are consistent with those used in the contemporary scientific literature, for example, the *Journal of the American Chemical Society or the Journal of Biological Chemistry*. Specifically, the following abbreviations may be used in the examples and throughout the specification:
g (grams); mg (milligrams);
L (liters); mL (milliliters);
µL (microliters); N (normal);
M (molar); mM (millimolar);
Hz (Hertz); MHz (megahertz);
mol (moles); mmol (millimoles);

rt (room temperature); min (minute);
h (hour); d (day);
MS (mass spec); LCMS (liquid chromatography mass spec);
GCMS (gas chromatography mass spec; ESI (electrospray ionization);
HPLC (high performance liquid chromatography);
psi (pounds per square inch); H₂ (hydrogen gas)
Pd(C) palladium on carbon; ee (enantiomeric excess);
NH₄Cl (ammonium chloride); THF (tetrahydrofuran);
MeCN (acetonitrile); CH₂Cl₂ (methylene chloride);
Pd(PPh₃)₄ (palladium tetrakistriphenyl phosphine);
NaOH (sodium hydroxide); TFA (trifluoroacetic acid);
CDCl₃ (deuterated chloroform); CD₃OD (deuterated methanol);
SiO₂ (silica); DMSO (dimethylsulfoxide);
EtOAc (ethyl acetate); Na₂SO₄ (sodium sulfate);
HCl (hydrochloric acid); CHCl₃ (chloroform);
DMF (N,N-dimethylformamide); PhMe (toluene);
Cs₂CO₃ (cesium carbonate); Me (methyl);
Et (ethyl); EtOH (ethanol);
MeOH (methanol); t-Bu (tert-butyl);
Et₂O (diethyl ether); N₂ (nitrogen);
sat'd (saturated); NaHCO₃ (sodium bicarbonate);
K₂CO₃ (potassium carbonate); Zn(CN)₂ (zinc cyanide);
NMP (N-methyl-2-pyrrolidone); DIEA (diisopropylethyl amine);
LiBH₄ (lithium borohydride); Et₃N (triethylamine);
Oxone (potassium peroxomonosulfate); LDA (lithium diisopropylamide);
Na₂S₂O₃ (sodium thiosulphate); DIPA (diisopropylamine);
PTFE (polytetrafluoroethylene); KOtBu (potassium t-butoxide);
hex (hexanes); semiprep (semipreparative);
NaCNBH₃ (sodium cyanoborohydride); CuI (copper iodode);
Pd(PPh₃)₂Cl₂ (bis(triphenylphosphine)palladiumchloride);
anhyd (anhydrous); DMAC (dimethyacetamide);
dppf (1,1'-bis(diphenylphosphino)ferrocene);
Pd₂(dba)₃ (tris(dibenzylideneacetone)dipalladium(0);
PMHS (polymethylhydrosiloxane); MsCl (mesyl chloride);
Aq (aqueous); TBAF (tetra-n-butylammonium fluoride)
n-BuLi (n-butyllithium); TsOH (tosic acid);
MTBE (methyl t-butyl ether); Boc₂O (di-t-butyl dicarbonate).

Unless otherwise indicated, all temperatures are expressed in ° C. (degrees Centigrade). All reactions conducted under an inert atmosphere at room temperature unless otherwise noted. Reagents employed without synthetic details are commercially available or made according to literature procedures.

UPLC-MS analysis was conducted on a Waters Acquity UPLC system using a Waters BEH C18 column with dimensions 2.1×50 mm at 40° C. A 0.5 uL partial loop with needle overfill injection was made, and UV detection was performed from 210 to 350 nm scanning at 40 Hz on a Waters Acquity PDA detector. A water+0.2% formic acid v/v (solvent A)/acetonitrile+0.15% formic acid v/v (solvent B) gradient was implemented with initial conditions 95/5% (A/B) to 1/99% over 1.10 min, and held until 1.5 min. A flow rate of 1 mL/min was used. Mass spectral analysis was performed on a Waters Acquity SQD with alternating positive/negative electrospray ionization scanning from 125-1000 amu, with a scan time of 105 msec, and an interscan delay of 20 msec.

¹H NMR spectra were acquired on a Varian Inova 400 MHz NMR spectrometer. The samples were dissolved in 99.9% Deuterated Chloroform-D, DMSO-d6, or d4-Methanol, as indicated for each sample. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or b (broad).

EXAMPLES

For the purposes of the following examples, when it is recited that a compound was "synthesized as described" in another example, it indicates that the compound was synthesized essentially as described in the other example with such modifications as are within the purview of the art.

Example 1

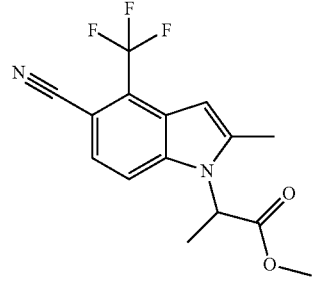 [SMILES: COC(=O)C(C)n1c(C)cc2c(C(F)(F)F)c(C#N)ccc21]

Methyl 2-[5-cyano-2-methyl-4-(trifluoromethyl)-1H-indol-1-yl]propanoate

A mixture of 2-methyl-4-(trifluoromethyl)-1H-indole-5-carbonitrile (see, for example, US2008139631A1) (0.300 g, 1.338 mmol), cesium carbonate (0.654 g, 2.007 mmol) and methyl 2-bromopropanoate (0.223 mL, 2.007 mmol) in DMF (3 mL) was heated at 90° C. for 1 h. Upon cooling, the reaction mixture was partitioned between Et₂O (30 mL) and water (25 mL). The organic phase was washed with water (20 mL) and brine (10 mL). The combined aqueous phases were washed with Et₂O (2×25 ml). The organic phases were combined, washed with brine, dried over Na₂SO₄, filtered and concentrated. The residue was chromatographed over silica gel eluting with 5-40% EtOAc-hexane gradient to give methyl 2-[5-cyano-2-methyl-4-(trifluoromethyl)-1H-indol-1-yl]propanoate (0.419 g, 94% yield): MS (ESI): m/z 311 (MH+).

Example 2

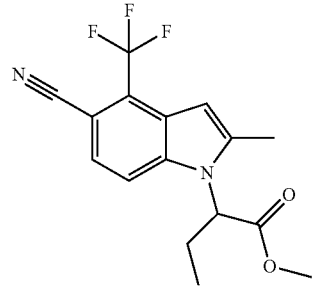 [SMILES: CCC(C(=O)OC)n1c(C)cc2c(C(F)(F)F)c(C#N)ccc21]

Methyl 2-[5-cyano-2-methyl-4-(trifluoromethyl)-1H-indol-1-yl]butanoate

Synthesized in a manner similar to Example 1 using 2-methyl-4-(trifluoromethyl)-1H-indole-5-carbonitrile and methyl 2-bromobutanoate: MS (ESI): m/z 325 (MH+).

Examples 3 and 4

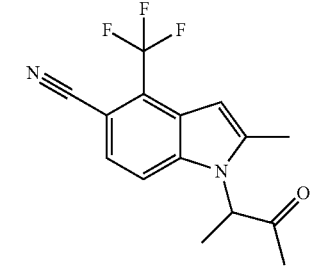

Ex. 3

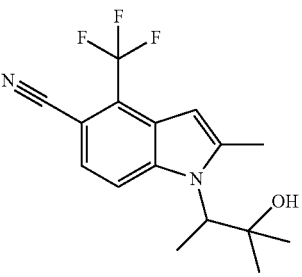

Ex. 4

2-Methyl-1-(1-methyl-2-oxopropyl)-4-(trifluoromethyl)-1H-indole-5-carbonitrile (Ex. 3) and 1-(2-Hydroxy-1,2-dimethylpropyl)-2-methyl-4-(trifluoromethyl)-1H-indole-5-carbonitrile (Ex. 4)

To an ice-cold solution of methyl magnesium iodide (3M in Et$_2$O) (0.322 ml, 0.967 mmol) in Et$_2$O (1 mL) was added a solution of methyl 2-[5-cyano-2-methyl-4-(trifluoromethyl)-1H-indol-1-yl]propanoate (Example 1) (0.100 g, 0.322 mmol) in Et$_2$O (1 mL). The heterogeneous mixture was stirred in an ice bath for 5 min, at rt for 10 min, and then at 38° C. for 1 h. Upon cooling, the reaction mixture was diluted with EtOAc (5 mL) and treated with aq. saturated NH$_4$Cl (5 mL). The mixture was partitioned between EtOAc (25 mL) and water (15 mL). The organic phase was washed with brine, dried over Na$_2$SO$_4$, filtered and concentrated. The residue was chromatographed over silica gel eluting sequentially with 50%, 75% and 100% CH$_2$Cl$_2$-hexanes to give 2-methyl-1-(1-methyl-2-oxopropyl)-4-(trifluoromethyl)-1H-indole-5-carbonitrile (0.008 g, 8% yield, less polar product) (MS (ESI): m/z 295 (MH+)) and 1-(2-hydroxy-1,2-dimethylpropyl)-2-methyl-4-(trifluoromethyl)-1H-indole-5-carbonitrile (0.069 g, 60% yield, more polar product) (MS (ESI): m/z 311 (MH+)).

Examples 5 and 6

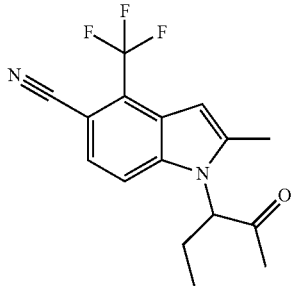

Ex. 5

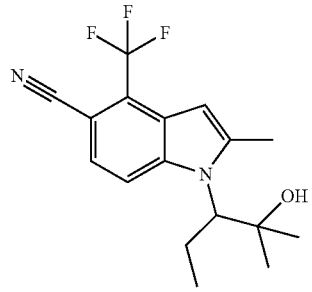

Ex. 6

1-(1-Ethyl-2-oxopropyl)-2-methyl-4-(trifluoromethyl)-1H-indole-5-carbonitrile (Ex. 5) and 1-(1-Ethyl-2-hydroxy-2-methylpropyl)-2-methyl-4-(trifluoromethyl)-1H-indole-5-carbonitrile (Ex. 6)

Synthesized in a manner similar to Examples 3 and 4 using methyl 2-[5-cyano-2-methyl-4-(trifluoromethyl)-1H-indol-1-yl]butanoate.

Example 5 (8% yield): 1-(1-Ethyl-2-oxopropyl)-2-methyl-4-(trifluoromethyl)-1H-indole-5-carbonitrile: MS (ESI): m/z 309 (MH+).

Example 6 (53% yield): 1-(1-Ethyl-2-hydroxy-2-methylpropyl)-2-methyl-4-(trifluoromethyl)-1H-indole-5-carbonitrile: MS (ESI): m/z 325 (MH+).

Example 7

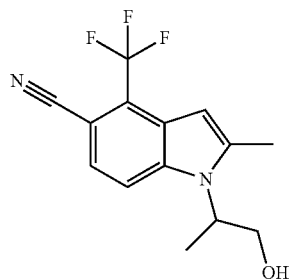 [SMILES: Cc1cc2c(C(F)(F)F)c(C#N)ccc2n1C(C)CO]

1-(1-Hydroxypropan-2-yl)-2-methyl-4-(trifluoromethyl)-1H-indole-5-carbonitrile

To an ice-cold solution of methyl 2-(5-cyano-2-methyl-4-(trifluoromethyl)-1H-indol-1-yl)propanoate (Example 1)

(0.263 g, 0.848 mmol) in THF (5 mL) was added dropwise LiBH₄ (2M in THF) (1.695 mL, 3.39 mmol). After complete addition of the reducing agent, the cold bath was removed and the mixture was stirred at rt. After 2 h, the reaction mixture was cooled in an ice bath and a saturated aqueous NH₄Cl solution (15 mL) was added slowly. The mixture was then diluted with EtOAc (40 mL) and treated slowly with 1N HCl (10 mL). The phases were separated and the aqueous phase was washed with EtOAc (20 mL). The combined organic phases were washed with brine, dried over Na₂SO₄, filtered and concentrated. The residue was chromatographed over silica gel using a 20-60% EtOAc-hexane gradient to give 1-(1-hydroxypropan-2-yl)-2-methyl-4-(trifluoromethyl)-1H-indole-5-carbonitrile (0.212 g, 83% yield) as a white solid: MS (ESI): m/z 283 (MH+).

Example 8

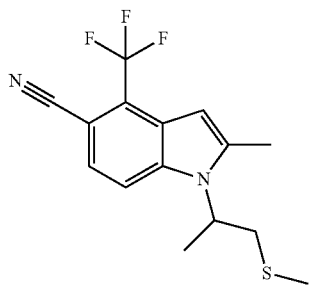 [SMILES: CSCC(C)n1c(C)cc2c(C(F)(F)F)c(C#N)ccc21]

2-Methyl-1-(1-(methylthio)propan-2-yl)-4-(trifluoromethyl)-1H-indole-5-carbonitrile

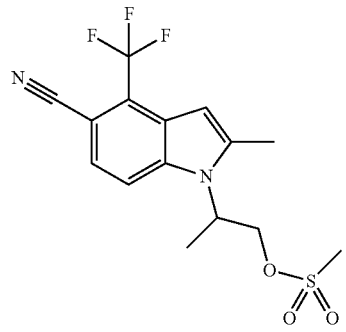 [SMILES: Cc1cc2c(C(F)(F)F)c(C#N)ccc2n1C(C)COS(C)(=O)=O]

A. 2-(5-Cyano-2-methyl-4-(trifluoromethyl)-1H-indol-1-yl)propyl methanesulfonate To a solution of 1-(1-hydroxypropan-2-yl)-2-methyl-4-(trifluoromethyl)-1H-indole-5-carbonitrile (Example 7) (0.110 g, 0.390 mmol) and Et₃N (0.068 mL, 0.487 mmol) in CH₂Cl₂ (4 mL) was added methanesulfonyl chloride (0.038 mL, 0.487 mmol) dropwise. After stirring at rt for 2 h, the reaction mixture was concentrated to dryness. The residue was partitioned between EtOAc (30 mL) and 0.2N HCl (15 mL). The organic phase was washed with water and brine, dried over Na₂SO₄, filtered and concentrated. The residue was chromatographed over silica gel using a 25-60% EtOAc-hexane gradient to give 2-(5-cyano-2-methyl-4-(tri- fluoromethyl)-1H-indol-1-yl)propyl methanesulfonate (0.145 g, 97% yield) as a colorless oil: MS (ESI): m/z 361 (MH+).

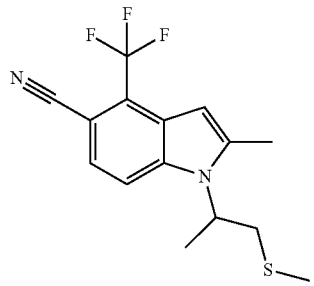 [SMILES: CSCC(C)n1c(C)cc2c(C(F)(F)F)c(C#N)ccc21]

B. 2-Methyl-1-(1-(methylthio)propan-2-yl)-4-(trifluoromethyl)-1H-indole-5-carbonitrile To a solution of 2-(5-cyano-2-methyl-4-(trifluoromethyl)-1H-indol-1-yl)propyl methanesulfonate (0.145 g, 0.402 mmol) in DMF (3 mL) was added sodium thiomethoxide (0.056 g, 0.805 mmol) in one portion. After 90 min, additional sodium thiomethoxide (2 eq) was added, and the mixture stirred for another 1 h. The reaction mixture was diluted with water (25 mL) and extracted with EtOAc (30 mL). The organic phase was washed with 0.1N HCl (1×20 mL) and brine, dried over Na₂SO₄, filtered and concentrated. The residue was chromatographed over silica gel using a 0-30% EtOAc-hexane gradient to give 2-methyl-1-(1-(methylthio)propan-2-yl)-4-(trifluoromethyl)-1H-indole-5-carbonitrile (0.094 g, 71% yield) as a colorless oil: MS (ESI): m/z 313 (MH+).

Example 9

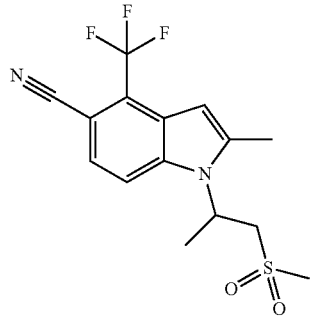 [SMILES: Cc1cc2c(C(F)(F)F)c(C#N)ccc2n1C(C)CS(C)(=O)=O]

2-Methyl-1-(1-(methylsulfonyl)propan-2-yl)-4-(trifluoromethyl)-1H-indole-5-carbonitrile To an ice-cold solution of 2-methyl-1-(1-(methylthio)propan-2-yl)-4-(trifluoromethyl)-1H-indole-5-carbonitrile (Example 8) (0.045 g, 0.144 mmol) in MeOH (4 mL) was added a solution of Oxone (0.133 g, 0.216 mmol) in water (2 mL). After 1 h, additional Oxone (0.100 g, 0.163 mmol) was added, and the mixture was stirred at rt. After 30 min, the reaction mixture was diluted with water (10 mL) and extracted with EtOAc (20 mL). The organic phase was washed with brine, dried over Na₂SO₄, filtered and concentrated. The residue was purified by preparative HPLC (Phenomenex Luna column; gradient: 10-100% MeCN-water with 0.1% TFA). The fractions with product were basified with aq. saturated K₂CO₃ solution, and then concentrated down to the aqueous phase, which was extracted with EtOAc. The organic phase was washed with brine, dried over Na₂SO₄, filtered and concentrated to give 2-methyl-1-(1-(methylsulfonyl)propan-2-yl)-4-(trifluoromethyl)-1H-indole-5-carbonitrile: MS (ESI): m/z 345 (MH+).

Example 10

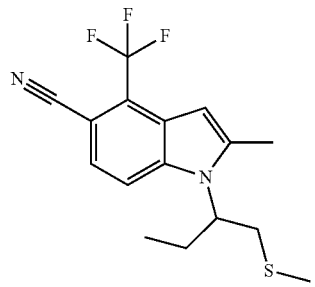 [SMILES: CCC(CSC)n1c(C)cc2c(C(F)(F)F)c(C#N)ccc21]

2-Methyl-1-(1-(methylthio)butan-2-yl)-4-(trifluoromethyl)-1H-indole-5-carbonitrile Synthesized in 3 steps, starting with methyl 2-[5-cyano-2-methyl-4-(trifluoromethyl)-1H-indol-1-yl]butanoate (Example 2) and using procedures similar to those described for Examples 7 and 8: MS (ESI): m/z 327 (MH+).

Example 11

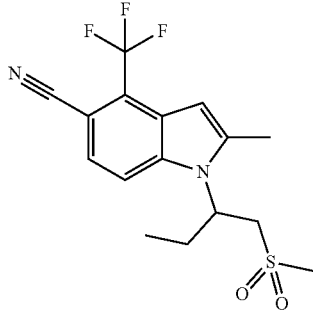 [SMILES: CCC(CS(C)(=O)=O)n1c(C)cc2c(C(F)(F)F)c(C#N)ccc21]

2-Methyl-1-(1-(methylsulfonyl)butan-2-yl)-4-(trifluoromethyl)-1H-indole-5-carbonitrile Synthesized in a manner similar to Example 9 using 2-methyl-1-(1-(methylthio)butan-2-yl)-4-(trifluoromethyl)-1H-indole-5-carbonitrile (Example 10): MS (ESI): m/z 359 (MH+).

Example 12

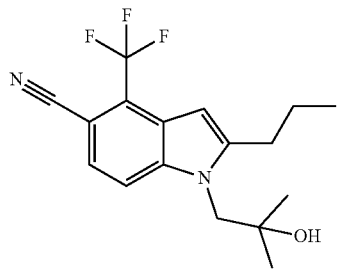 [SMILES: CCCc1cc2c(C(F)(F)F)c(C#N)ccc2n1CC(C)(C)O]

1-(2-Hydroxy-2-methylpropyl)-2-propyl-4-(trifluoromethyl)-1H-indole-5-carbonitrile A mixture of 2-propyl-4-(trifluoromethyl)-1H-indole-5-carbonitrile (0.025 g, 0.099 mmol) (see, for example, US2008139631A1), Cs₂CO₃ (0.129 g, 0.396 mmol), potassium iodide (0.0165 g, 0.099 mmol) and commercially available 1-chloro-2-methylpropan-2-ol (0.041 mL, 0.396 mmol) in DMF (2 mL) was heated at 80° C. for 90 min and then at 120° C. for 1 h. Additional 1-chloro-2-methylpropan-2-ol (0.041 mL, 0.396 mmol), Cs₂CO₃ (0.129 g, 0.396 mmol) and potassium iodide (0.0165 g, 0.099 mmol) were added, and heating continued at 120° C. for another 6 h. Upon cooling, the mixture was partitioned between EtOAc (25 mL) and water (20 mL). The organic phase was washed with water and brine, dried over Na₂SO₄, filtered, and concentrated. The residue was purified by preparative HPLC (Phenomenex Luna column; gradient: 10-90% MeCN-water with 0.1% TFA). The fractions with product were concentrated down to the aqueous phase, which is then partitioned between EtOAc (25 mL) and saturated aqueous NaHCO₃ solution (20 mL). The organic phase was washed with brine, dried over Na₂SO₄, filtered and concentrated. This chromatography did not separate product from unreacted starting indole, so the material was chromatographed over silica gel using a 50%-100% CH₂Cl₂-hexanes gradient to give 1-(2-(methylthio)ethyl)-2-propyl-4-(trifluoromethyl)-1H-indole-5-carbonitrile (0.014 g, 42% yield) as a white solid: MS (ESI): m/z 325 (M+H).

Example 13

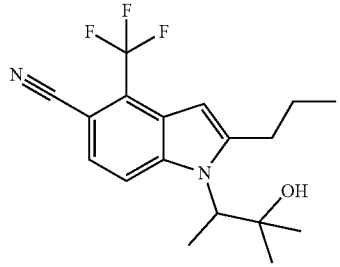 [SMILES: CCCc1cc2c(C(F)(F)F)c(C#N)ccc2n1C(C)C(C)(C)O]

1-(3-Hydroxy-3-methyl butan-2-yl)-2-propyl-4-(trifluoromethyl)-1H-indole-5-carbonitrile

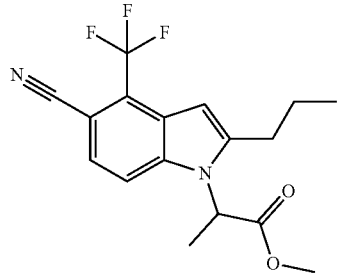 [SMILES: CCCc1cc2c(C(F)(F)F)c(C#N)ccc2n1C(C)C(=O)OC]

A. Methyl 2-(5-cyano-2-propyl-4-(trifluoromethyl)-1H-indol-1-yl)propanoate

Synthesized in a manner similar to Example 1 using 2-propyl-4-(trifluoromethyl)-1H-indole-5-carbonitrile and methyl 2-bromopropanoate: MS (ESI): m/z 339 (MH+).

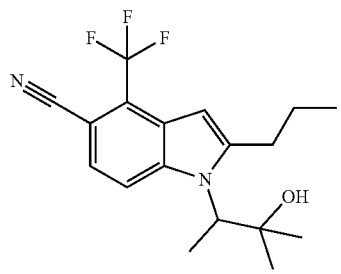 [SMILES: CCCc1cc2c(C(F)(F)F)c(C#N)ccc2n1C(C)C(C)(C)O]

B. 1-(3-Hydroxy-3-methylbutan-2-yl)-2-propyl-4-(trifluoromethyl)-1H-indole-5-carbonitrile Synthesized in a manner similar to Example 4 using methyl 2-(5-cyano-2-propyl-4-(trifluoromethyl)-1H-indol-1-yl)propanoate: MS (ESI): m/z 339 (MH+).

Example 14

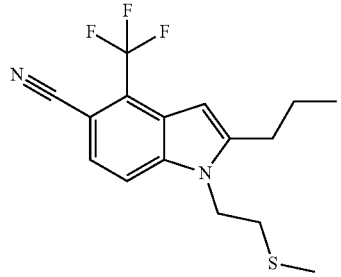 [SMILES: CCCc1cc2c(C(F)(F)F)c(C#N)ccc2n1CCSC]

1-(2-(Methylthio)ethyl)-2-propyl-4-(trifluoromethyl)-1H-indole-5-carbonitrile

A mixture of 2-propyl-4-(trifluoromethyl)-1H-indole-5-carbonitrile (0.025 g, 0.099 mmol), Cs₂CO₃ (0.129 g, 0.396 mmol), (2-chloroethyl)(methyl)sulfane (0.039 mL, 0.396 mmol) and potassium iodide (0.0165 g, 0.099 mmol) in DMF (2 mL) was heated at 80° C. After ~1 h, additional Cs₂CO₃ (0.129 g, 0.396 mmol), (2-chloroethyl)(methyl)sulfane (0.039 mL, 0.396 mmol) and potassium iodide (0.0165 g, 0.099 mmol) were added, and heating was continued for 1 h. Upon cooling, the mixture was partitioned between EtOAc (25 mL) and water (20 mL). The organic phase was washed with water and brine, dried over Na₂SO₄, filtered and concentrated. The residue was purified by preparative HPLC (Phenomenex Luna column; gradient: 10-90% MeCN-water with 0.1% TFA). The fractions with product were concentrated down to the aqueous phase and then partitioned between EtOAc (25 mL) and saturated aqueous NaHCO₃ solution (20 mL). The organic phase was washed with brine, dried over Na₂SO₄, filtered and concentrated to give 1-(2-(methylthio)ethyl)-2-propyl-4-(trifluoromethyl)-1H-indole-5-carbonitrile: MS (ESI): m/z 327 (M+H).

Example 15

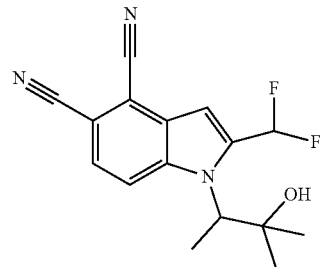 [SMILES: CC(n1c(C(F)F)cc2c(C#N)c(C#N)ccc21)C(C)(C)O]

1-(1-(Methylthio)propan-2-yl)-2-propyl-4-(trifluoromethyl)-1H-indole-5-carbonitrile Synthesized in 3 steps, starting with methyl 2-(5-cyano-2-propyl-4-(trifluoromethyl)-1H-indol-1-yl)propanoate (Example 13A) using procedures similar to those described for Examples 7 and 8: MS (ESI): m/z 341 (M+H).

Example 16

2-(Difluoromethyl)-1-(3-hydroxy-3-methylbutan-2-yl)-1H-indole-4,5-dicarbonitrile

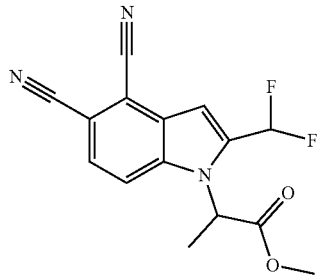 [SMILES: COC(=O)C(C)n1c(C(F)F)cc2c(C#N)c(C#N)ccc21]

A. Methyl 2-(4,5-dicyano-2-(difluoromethyl)-1H-indol-1-yl)propanoate

Synthesized in a manner similar to Example 1 using 2-(difluoromethyl)-1H-indole-4,5-dicarbonitrile (see, for example, US2008139631A1) and methyl 2-bromopropanoate: MS (ESI): m/z 304 (M+H).

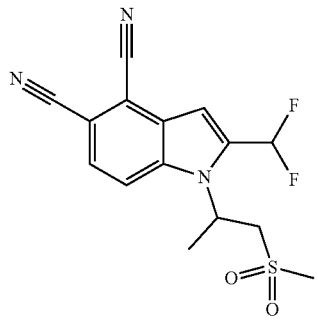

B. 2-(Difluoromethyl)-1-(3-hydroxy-3-methylbutan-2-yl)-1H-indole-4,5-dicarbonitrile Synthesized in a manner similar to Example 4 using methyl 2-(4,5-dicyano-2-(difluoromethyl)-1H-indol-1-yl)propanoate: MS (ESI): m/z 304 (M+H).

Example 17

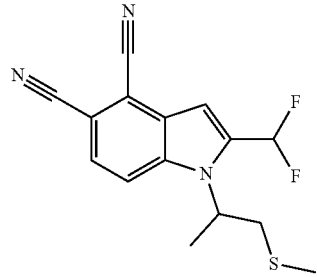 [SMILES: CSCC(C)n1c(C(F)F)cc2c(C#N)c(C#N)ccc21]

2-(Difluoromethyl)-1-(1-(methylthio)propan-2-yl)-1H-indole-4,5-dicarbonitrile

Synthesized in 3 steps, starting with methyl 2-(4,5-dicyano-2-(difluoromethyl)-1H-indol-1-yl)propanoate (Example 16A) using procedures similar to those described for Examples 7 and 8: MS (ESI): m/z 306 (M+H).

Example 18

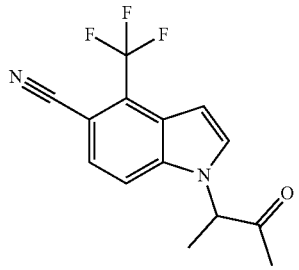

2-(Difluoromethyl)-1-(1-(methylsulfonyl)propan-2-yl)-1H-indole-4,5-dicarbonitrile Synthesized in a manner similar to Example 9 using 2-(difluoromethyl)-1-(1-(methylthio)propan-2-yl)-1H-indole-4,5-dicarbonitrile (Example 17): MS (ESI): m/z 338 (M+H).

Examples 19 and 20

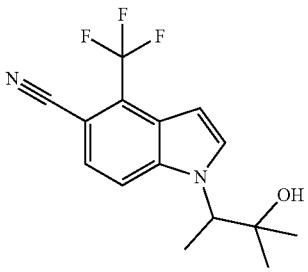

1-(3-Oxobutan-2-yl)-4-(trifluoromethyl)-1H-indole-5-carbonitrile (Ex. 19) and 1-(3-Hydroxy-3-methylbutan-2-yl)-4-(trifluoromethyl)-1H-indole-5-carbonitrile (Ex. 20)

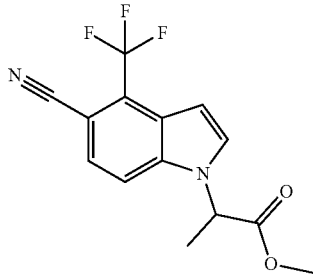 [SMILES: COC(=O)C(C)n1ccc2c(C(F)(F)F)c(C#N)ccc21]

A. Methyl 2-(5-cyano-4-(trifluoromethyl)-1H-indol-1-yl)propanoate

Synthesized in a manner similar to Example 1 using 4-(trifluoromethyl)-1H-indole-5-carbonitrile (see, for example, US2008139631A1) and methyl 2-bromopropanoate: MS (ESI): m/z 297 (MH+).

Ex. 19
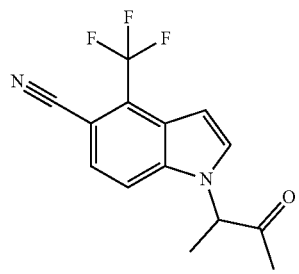

Ex. 20
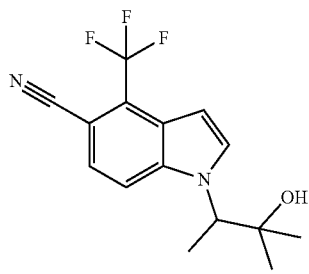

B. 1-(3-Oxobutan-2-yl)-4-(trifluoromethyl)-1H-indole-5-carbonitrile (Ex. 19) and 1-(3-Hydroxy-3-methylbutan-2-yl)-4-(trifluoromethyl)-1H-indole-5-carbonitrile (Ex. 20)

Synthesized in a manner similar to Examples 3 and 4 using methyl 2-(5-cyano-4-(trifluoromethyl)-1H-indol-1-yl)propanoate.

Example 19 (8% yield): 1-(3-oxobutan-2-yl)-4-(trifluoromethyl)-1H-indole-5-carbonitrile: MS (ESI): m/z 281 (MH+).

Example 20 (53% yield): 1-(3-hydroxy-3-methylbutan-2-yl)-4-(trifluoromethyl)-1H-indole-5-carbonitrile: MS (ESI): m/z 297 (MH+).

Example 21

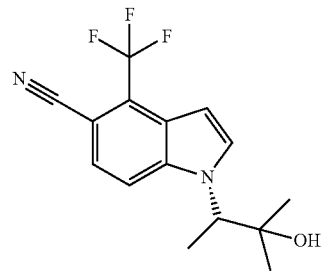

(S)-1-(3-Hydroxy-3-methyl butan-2-yl)-4-(trifluoromethyl)-1H-indole-5-carbonitrile

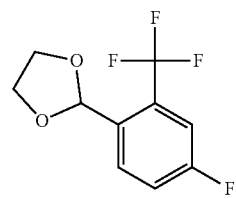 [SMILES: Fc1ccc(C2OCCO2)c(C(F)(F)F)c1]

A. 2-(4-Fluoro-2-(trifluoromethyl)phenyl)-1,3-dioxolane

To a solution of commercially available 4-fluoro-2-(trifluoromethyl)benzaldehyde (15 g, 78 mmol) in toluene (90 mL) was added ethylene glycol (21.77 mL, 390 mmol) and TsOH (0.743 g, 3.90 mmol). The mixture was then heated (under a Dean-Stark trap attached to a reflux condenser) in an oil bath at 140° C. for 4 h, about 1.4-1.5 mL of water was collected, which was close to the expected volume. TLC (20% EtOAc-hexane) showed a major, new more polar spot. The mixture is diluted with EtOAc (100 mL) and washed with water (50 mL). The organic phase is washed with water (1×50 mL) and brine (50 mL), dried over Na$_2$SO$_4$, filtered and concentrated. The residue was purified by silica gel column chromatography (330 g ISCO column) eluting with 0-10% EtOAc-hexane gradient. The cleanest fractions with product afforded 9.83 g (51% yield): MS (ESI): m/z 237 (M+H).

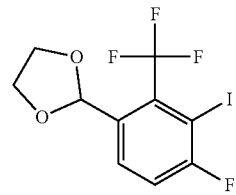 [SMILES: Fc1ccc(C2OCCO2)c(C(F)(F)F)c1I]

B. 2-(4-Fluoro-3-iodo-2-(trifluoromethyl)phenyl)-1,3-dioxolane

To a solution of 2-(4-fluoro-2-(trifluoromethyl)phenyl)-1,3-dioxolane (2.52 g, 10.65 mmol) and DIPA (0.150 mL, 1.067 mmol) in anhyd THF (30 mL) at −78° C. was added a solution of n-BuLi in hexanes (4.26 mL, 10.65 mmol), dropwise at such a rate that the internal temperature remained <−70° C. The resulting pale yellow solution was stirred 3 h at −78° C. during which time a blue color developed. Iodine (2.97 g, 11.71 mmol) was added in one portion (internal temp −78° C.→−66° C.). The mixture was stirred 30 min, removed from the cooling bath and quenched by addition of 10% Na₂S₂O₃. Upon warming, the mixture was poured into water and extracted with EtOAc (×3). Combined organics were washed (water, brine), dried over Na₂SO₄ and concentrated in vacuo. The residue was purified by low pressure liquid chromatography (silica gel, EtOAc/hexanes, gradient elution) affording 2.49 g of a mixture of desired product and unreacted starting material (ca. 9:1 by ¹H NMR). The mixture was resolved by reversed phase low pressure liquid chromatography (C18 column, MeOH/water gradient) affording 2-(4-fluoro-3-iodo-2-(trifluoromethyl)phenyl)-1,3-dioxolane (2.13 g, 5.88 mmol, 55.2% yield) as a pale yellow oil: 1H NMR (400 MHz, CDCl₃) δ ppm 7.87 (dd, J=8.8, 5.7 Hz, 1H) 7.23 (m, J=8.2, 7.5, 0.6, 0.6 Hz, 1H), 6.23 (q, J=2.1 Hz, 1H), 4.10-4.03 (m, 4H).

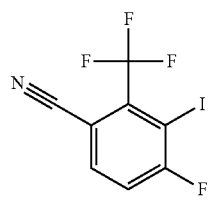 [SMILES: N#Cc1ccc(F)c(I)c1C(F)(F)F]

C. 4-Fluoro-3-iodo-2-(trifluoromethyl)benzonitrile

Step 1

To a solution of 2-(4-fluoro-3-iodo-2-(trifluoromethyl)phenyl)-1,3-dioxolane (9.43 g, 26.0 mmol) in acetone (60 mL) was added aqueous hydrochloric acid (52.1 mL, 52.1 mmol) and the mixture was heated under reflux for 15 h (complete conversion by ¹H NMR). The mixture was cooled, slowly poured into satd NaHCO₃ and extracted with EtOAc (×3). Combined organics were washed (water, brine), dried over Na₂SO₄ and concentrated in vacuo affording 8.09 g pale yellow syrup which crystallized on standing (assume 25.4 mmol benzaldehyde).

Step 2

To a solution of benzaldehyde from step 1 and Et₃N (7.08 mL, 50.8 mmol) in chloroform (75 mL) was added hydroxylamine hydrochloride (1.864 g, 26.8 mmol) in one portion and the mixture was stirred at rt. An additional portion of hydroxylamine hydrochloride (0.441 g; 6.35 mmol) was added after 3 h and stirring was continued overnight. ¹H NMR after 18 h indicated complete conversion to the oxime.

Step 3

To the solution from step 2 was added Et₃N (7.08 mL, 50.8 mmol) and the mixture was cooled in an ice bath. A solution of triphosgene (8.27 g, 27.9 mmol) in chloroform (20 mL) was added dropwise over 15 min. ¹H NMR after 1 h, indicated complete conversion. The mixture was washed (water×2, NaHCO₃, brine), dried over Na₂SO₄ and concentrated in vacuo. The crude solid obtained was recrystallized from heptane affording 4-fluoro-3-iodo-2-(trifluoromethyl)benzonitrile (5.88 g, 18.67 mmol, 71.7% yield) as a pale yellow solid: ¹H NMR (400 MHz, CDCl₃) δ 7.85 (ddd, J=8.6, 5.1, 0.5 Hz, 1H), 7.36 (ddd, J=8.6, 6.6, 0.5 Hz, 1H); MS (GCMS EI) m/z 315 ([M]⁺, 100%).

Alternative Route to Example 21C

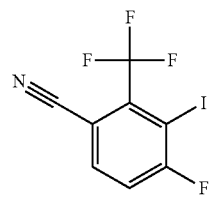 [SMILES: N#Cc1ccc(F)c(I)c1C(F)(F)F]

4-Fluoro-3-iodo-2-(trifluoromethyl)benzonitrile

To a freshly prepared solution of LDA (119 mmol) in anhyd THF (250 mL) at −45° C. was added a solution of commercially available 4-fluoro-2-(trifluoromethyl)benzonitrile (21.5 g, 114 mmol) in THF (30 mL), dropwise at a rate such that the internal temperature remained <−40° C. (became dark brown during addition). The mixture was stirred 30 min at −45° C., cooled to −70° C. and iodine (31.7 g, 125 mmol) was added in one portion (−70° C.→−52° C.). The mixture was stirred for 1 h, removed from the cooling bath and quenched by addition of 10% Na₂S₂O₃ (ca. 250 mL) and 1N HCl (ca. 125 mL). The mixture was extracted with EtOAc (×3). Combined organics were washed (water, brine), dried over Na₂SO₄ and concentrated in vacuo. The residue was purified by low pressure liquid chromatography (silica gel, EtOAc/hexanes, gradient elution) followed by recrystallization from heptane (30 mL), twice, affording 4-fluoro-3-iodo-2-(trifluoromethyl)benzonitrile (15.79 g, 50.1 mmol, 44.1% yield) as a pale yellow solid: ¹H NMR (400 MHz, CDCl₃) δ 7.85 (ddd, J=8.6, 5.1, 0.5 Hz, 1H), 7.36 (ddd, J=8.6, 6.6, 0.5 Hz, 1H); MS (GCMS EI) m/z 315 ([M]⁺, 100%).

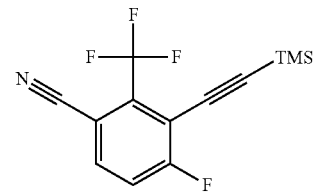 [SMILES: C[Si](C)(C)C#Cc1c(F)ccc(C#N)c1C(F)(F)F]

D. 4-Fluoro-2-(trifluoromethyl)-3-((trimethylsilyl)ethynyl)benzonitrile

A 20 mL vial was charged with 4-fluoro-3-iodo-2-(trifluoromethyl)benzonitrile, (0.315 g, 1.00 mmol), Pd(PPh₃)₂Cl₂ (0.014 g, 0.020 mmol) and CuI (0.0076 g, 0.040 mmol), and sealed with a rubber septum. Anhyd PhMe (5 mL) and DIPA (0.210 mL, 1.500 mmol) were added via syringe and the mixture was degassed 10 min by sparging with N₂ while immersed in an ultrasonic bath. Ethynyltrimethylsilane (0.155 mL, 1.100 mmol) was added dropwise via syringe and the septum was replaced by a PTFE-faced crimp top. The mixture was stirred in a heating block at 60° C. Upon cooling the mixture was diluted with EtOAc and filtered through Celite. The filtrate was washed (satd NH₄Cl, water, brine), dried over Na₂SO₄ and concentrated in vacuo. The residue was purified by low pressure liquid chromatography (silica gel, EtOAc/hexanes, gradient elution) affording 4-fluoro-2-(trifluoromethyl)-3-((trimethylsilyl)ethynyl)benzonitrile (0.231 g, 81% yield) as a light orange oil: $^1$H NMR (400 MHz, CDCl$_3$) δ 7.75 (ddd, J=8.7, 5.0, 0.6 Hz, 1H), 7.39 (ddd, J=8.6, 7.8, 0.5 Hz, 1H), 0.28 (s, 9H); MS (GCMS EI) m/z 285 ([M]$^+$, 15%), 270 ([M-CH$_3$]$^+$, 100%).

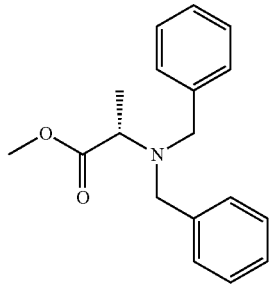 [SMILES: COC(=O)[C@H](C)N(Cc1ccccc1)Cc1ccccc1]

E. (S)-Methyl 2-(dibenzylamino)propanoate

Commercially available (S)-methyl 2-aminopropanoate, hydrochloride (10.0 g, 71.6 mmol) was suspended in DMF (35 mL) and then K$_2$CO$_3$ (31.7 g. 229 mmol) was added followed by benzyl bromide (18.21 mL, 158 mmol). The mixture was left to stir for 38 h at rt. LCMS showed good conversion to the desired product at this time. The reaction was filtered and the solid components were rinsed with EtOAc. The filtrate was then diluted with water and EtOAc and the layers were partitioned. The aqueous portion was extracted with small portions of EtOAc. The combined organic portions were dried over Na$_2$SO$_4$, filtered, and concentrated to a pale yellow, viscous oil. This oil was then chromatographed (ISCO, silica 120 g column, 254 collection, general gradient; hexanes/EtOAc) to afford the desired product (15.76 g, 75%): MS (ESI) m/z 284 (M+H).

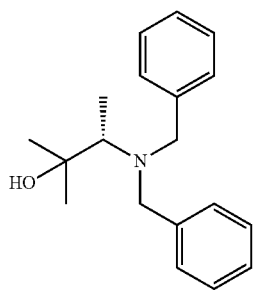 [SMILES: C[C@H](N(Cc1ccccc1)Cc1ccccc1)C(C)(C)O]

F. (S)-3-(Dibenzylamino)-2-methylbutan-2-ol (S)-Methyl 2-(dibenzylamino)propanoate (15.76 g, 55.6 mmol) was dissolved in Et$_2$O (400 mL) and then cooled to ca. 0° C. Methylmagnesium iodide (27.7 mL, 3 M) was added next. The mixture turned heterogeneous white with addition of the latter. The mixture was allowed to warm to ambient temperature. LCMS the next day (17 h) indicated conversion to the desired product. The reaction was slowly quenched with sat. aqueous NH$_4$Cl and then diluted with water and EtOAc. The layers were separated and the aqueous portion was further extracted with EtOAc. The combined organic portions were dried over Na$_2$SO$_4$, filtered and concentrated to a pale yellow oil. LCMS after thorough drying showed the desired product. This material was used directly for the next step: MS (ESI) m/z 284 (M+1).

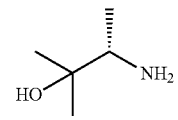

G. (S)-3-Amino-2-methylbutan-2-ol

S)-3-(Dibenzylamino)-2-methylbutan-2-ol (15.76 g, 55.6 mmol) was dissolved in MeOH (250 mL) and then treated with Pd(C) (2.0 g, 10% dry weight, 50% water). The reaction vessel was then purged with N$_2$ and vacuum cycles (7×) and then charged with H$_2$ (two vacuum and charge cycles) to 65 psi on a Fischer Porter apparatus. The vessel pressure was held at 65 psi for the first 2 h with charging as needed. The pressure held after 2 h. The reaction was left to stir at ambient temperature overnight. The reaction vessel was purged with alternating cycles of vacuum and N$_2$. The catalyst was filter away with Celite and the cake was rinsed with MeOH. Water was added to the spent cake to minimize fire potential. The filtrate was carefully concentrated to a pale yellow, thick liquid (5.60 g, 98%) via rotavap (40 torr 45° C.) followed by high vac. $^1$HNMR confirmed the absence of methanol. Excessive exposure to high vacuum will result in loss of product: $^1$H NMR (400 MHz, DMSO-d$_6$) δ 4.12 (bs, 1H), 2.57 (q, J=6.5 Hz, 1H), 1.40 (bs, 2H), 1.03 (s, 3H), 1.00 (s, 3H), 0.90 (d, J=6.7 Hz, 3H).

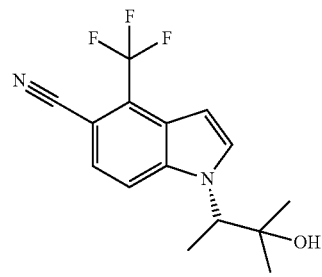

H. (S)-1-(3-Hydroxy-3-methylbutan-2-yl)-4-(trifluoromethyl)-1H-indole-5-carbonitrile 4-Fluoro-2-(trifluoromethyl)-3-((trimethylsilyl)ethynyl) benzonitrile (0.063 g, 0.221 mmol), (S)-3-amino-2-methylbutan-2-ol (0.060 g, 0.582 mmol) and DIEA (0.077 mL, 0.442 mmol) were combined in NMP (0.5 mL) and heated to 90° C. LCMS after heating for 9 h showed good conversion to the aniline intermediate and some desired indole formation. The mixture was cooled to rt and then treated with KOtBu (1.98 mL, 1 M in THF). The base did not afford conversion to the desired indole despite heating. The mixture was quenched with sat. aqueous NH$_4$Cl, and then extracted with EtOAc. The combined organic fractions were concentrated to a yellow oil and then diluted with NMP (1 mL). Addition of more KOtBu (1.98 mL, 1 M in THF) afforded a dark brown solution that was heated to 50° C. LCMS after 0.5 h showed conversion to the desired indole. The reaction was again quenched with sat. aqueous NH$_4$Cl and then extracted with EtOAc. The combined organic portions were concentrated to a yellow oil and then chromatographed (ISCO, std grad, hex/EtOAc, 24 g silica) to afford the desired product. The mixture was next subjected to reverse phase semiprep (Agilent, 230 nm detection) to afford the desired product as a colorless gum: MS (ESI): m/z 297 (MH+).

Example 22

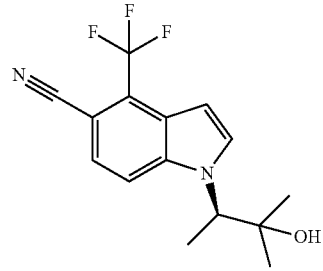 [SMILES: C[C@@H](n1ccc2c(C(F)(F)F)c(C#N)ccc21)C(C)(C)O]

(R)-1-(3-Hydroxy-3-methylbutan-2-yl)-4-(trifluoromethyl)-1H-indole-5-carbonitrile Synthesized in a manner similar to Example 21 staring with commercially available (R)-methyl 2-aminopropanoate, hydrochloride: MS (ESI): m/z 297 (MH+).

Example 23

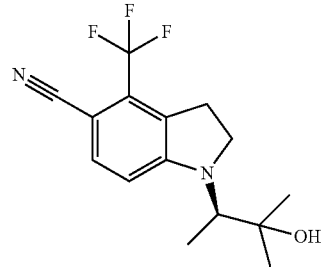 [SMILES: C[C@@H](N1CCc2c1ccc(C#N)c2C(F)(F)F)C(C)(C)O]

(R)-1-(3-Hydroxy-3-methylbutan-2-yl)-4-(trifluoromethyl)indoline-5-carbonitrile

To a solution of (R)-1-(3-hydroxy-3-methylbutan-2-yl)-4-(trifluoromethyl)-1H-indole-5-carbonitrile (Example 22) (0.017 g, 0.057 mmol) in TFA (1.5 mL), in an ice bath, was added NaCNBH$_3$ (0.0721 g, 1.148 mmol) in portions. After stirring in the cold bath for 1 h, the reaction mixture was partially concentrated. The residue was dissolved in CH$_2$Cl$_2$ (20 mL) and washed with 0.5 N NaOH (10 mL). The organic phase was washed with 0.5 N NaOH (1×10 mL) and brine, dried over Na$_2$SO$_4$, filtered and concentrated. The residue was chromatographed over silica gel using a 10-40% EtOAc-hexane gradient to give (R)-1-(3-hydroxy-3-methylbutan-2-yl)-4-(trifluoromethyl)indoline-5-carbonitrile: MS (ESI): m/z 299 (M+H).

Example 24

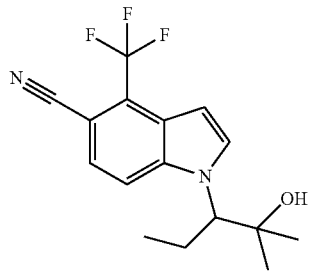 [SMILES: CCC(n1ccc2c(C(F)(F)F)c(C#N)ccc21)C(C)(C)O]

1-(2-Hydroxy-2-methylpentan-3-yl)-4-(trifluoromethyl)-1H-indole-5-carbonitrile

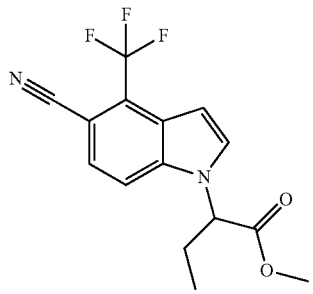 [SMILES: CCC(C(=O)OC)n1ccc2c(C(F)(F)F)c(C#N)ccc21]

A. Methyl 2-(5-cyano-4-(trifluoromethyl)-1H-indol-1-yl)butanoate

Synthesized in a manner similar to Example 1 using 4-(trifluoromethyl)-1H-indole-5-carbonitrile and methyl 2-bromobutanoate: MS (ESI): m/z 311 (MH+).

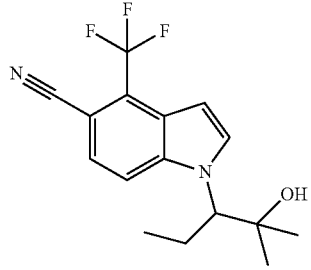 [SMILES: CCC(n1ccc2c(C(F)(F)F)c(C#N)ccc21)C(C)(C)O]

B. 1-(2-Hydroxy-2-methyl pentan-3-yl)-4-(trifluoromethyl)-1H-indole-5-carbonitrile Synthesized in a manner similar to Example 4 using methyl 2-(5-cyano-4-(trifluoromethyl)-1H-indol-1-yl)butanoate: MS (ESI): m/z 311 (MH+).

Example 25

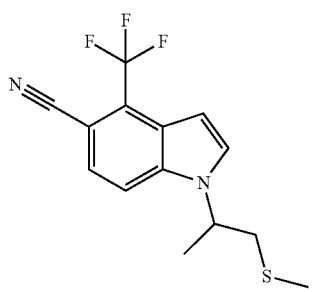 [SMILES: CSCC(C)n1ccc2c(C(F)(F)F)c(C#N)ccc21]

1-(1-(Methylthio)propan-2-yl)-4-(trifluoromethyl)-1H-indole-5-carbonitrile

Synthesized in 3 steps, starting with methyl 2-(5-cyano-4-(trifluoromethyl)-1H-indol-1-yl)propanoate (Example 19A) using procedures similar to those described for Examples 7 and 8: MS (ESI): m/z 299 (MH+).

Example 26

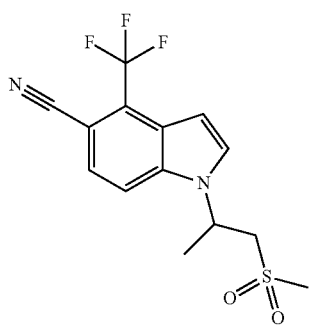 [SMILES: CC(CS(C)(=O)=O)n1ccc2c(C(F)(F)F)c(C#N)ccc21]

1-(1-(Methylsulfonyl)propan-2-yl)-4-(trifluoromethyl)-1H-indole-5-carbonitrile

Synthesized in a manner similar to Example 9 using 1-(1-(methylthio)propan-2-yl)-4-(trifluoromethyl)-1H-indole-5-carbonitrile (Example 25): MS (ESI): m/z 331 (MH+).

Example 27

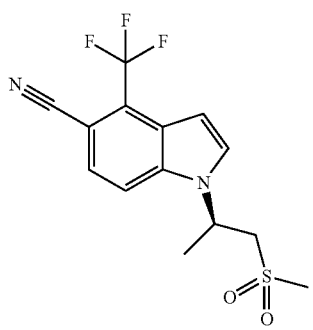 [SMILES: C[C@H](CS(C)(=O)=O)n1ccc2c(C(F)(F)F)c(C#N)ccc21]

(R)-1-(1-(Methylsulfonyl)propan-2-yl)-4-(trifluoromethyl)-1H-indole-5-carbonitrile

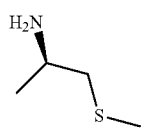

A. (R)-1-(Methylthio)propan-2-amine

Step 1

To a solution of commercially available (R)-2-aminopropan-1-ol (5 g, 66.6 mmol) in MeCN (20 mL), in an ice bath, was added very slowly, dropwise, chlorosulfonic acid (4.46 mL, 66.6 mmol) (very exothermic). A gummy beige precipitate formed. The reaction mixture was kept in the cold bath for ~10 min, and then at rt for ~30 min. The reaction mixture was scratched with a spatula to try to solidify the gummy precipitate. After a few minutes, a beige solid formed. After stirring for another ~10 minutes, the solids were collected by filtration, washed sequentially with MeCN (40 mL) and hexanes (100 mL), and dried by air suction for ~40 min. The intermediate ((R)-2-aminopropyl hydrogen sulfate, weighed 0.46 g (~96% yield).

Step 2:

To a solution of sodium thiomethoxide (5.60 g, 80 mmol) in water (20 mL) was added solid NaOH (2.66 g, 66.6 mmol) in portions over ~10 min. Then the intermediate from step 1 was added as a solid over ~5 min. The mixture was then heated at 90° C. for ~10 h. The reaction mixture was biphasic. Upon cooling, MTBE (20 mL) was added, and the organic phase (brownish color) was separated. The aqueous phase was extracted with MTBE (2×20 mL). The original organic phase is washed with 1N NaOH (15 mL) (this removes most of the color). The basic aqueous phase was re-extracted with MTBE (2×20 mL). All the ether phases are combined, dried over Na$_2$SO$_4$, filtered, and concentrated (carefully, since the product is volatile) to afford the crude product as a light yellow oil: $^1$H NMR (400 MHz, DMSO-d$_6$) δ 2.91-2.87 (m, 1H), 2.43-2.31 (m, 2H), 2.04 (s, 3H), 1.50 (bs, 2H), 1.01 (d, J=6.3 Hz, 3H).

Alternative Synthesis of Example 27A

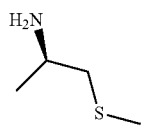

43

(R)-1-(Methylthio)propan-2-amine hydrochloride

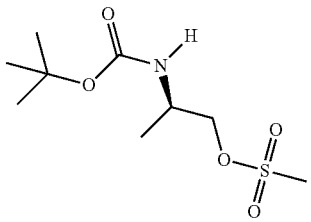 [SMILES: C[C@H](COS(C)(=O)=O)NC(=O)OC(C)(C)C]

A. (R)-2-((tert-Butoxycarbonyl)amino)propyl methanesulfonate

Step 1

Commercially available (R)-2-aminopropan-1-ol (135 g, 1797 mmol) was dissolved in MeOH 1350 mL). The solution was cooled to 5° C. with an icebath, then Boc$_2$O (392 g, 1797 mmol) was added as a solution in MeOH (1000 mL). The reaction temperature was kept below 10° C. After the addition, the cooling bath was removed, and the mixture was stirred for 3 h. The MeOH was removed under vacuum (rotavap bath: 50° C.). The resulting residue was a colorless oil that solidified overnight to a white solid. This material was used as is for the next step.

Step 2

The residue was dissolved in CH$_2$Cl$_2$ (1200 mL) and NEt$_3$ (378 mL, 2717 mmol) was added, then the mixture was cooled on an ice bath. Next, MsCl (166.5 mL, 2152 mmol) was added over ~2 h, while keeping the reaction temperature below 15° C. The mixture was stirred in an icebath for 1 h then the bath was removed. The mixture was stirred for 3 d, then washed with a 10% NaOH solution (500 mL 3×), then with water. The organic phase was dried with MgSO$_4$, filtered, then stripped off (rota, 50° C. waterbath. The impure residue was dissolved in a mix of 500 mL EtOAc (500 mL) and MTBE (500 mL) and then. extracted with water to remove all water-soluble salts. The organic phase was dried with MgSO$_4$, filtered, then stripped off to afford a white solid residue: $^1$H NMR (400 MHz, DMSO-d$_6$) δ 6.94-6.92 (m, 1H), 4.02 (d, J=5.8 Hz, 2H), 3.78-3.71 (m, 1H), 3.16 (s, 3H), 1.38 (s, 9H), 1.06 (d, J=6.8 Hz, 3H).

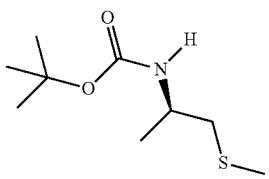

B. (R)-tert-Butyl (1-(methylthio)propan-2-yl)carbamate

NaSMe (30 g, 428 mmol) was stirred with DMF (200 mL) to afford a suspension. Next, (R)-2-((tertbutoxycarbonyl)amino)propyl methanesulfonate (97 g, 383 mmol) was added portionwise while the temperature was kept below 45° C. (exothermic). After the addition, the mixture was stirred for 2 h, then toluene (100 mL) was added. The mixture was washed with water (500 mL, 4×), then dried with MgSO$_4$, and filtered. The filtrate was stripped off (rotavap) to a pale yellow oil: $^1$H NMR (400 MHz, DMSO-d$_6$) δ 6.77-6.75 (m, 1H), 3.60-3.54 (m, 1H), 2.54-2.50 (m, 1H), 2.43-2.38 (m, 1H), 2.05 (s, 3H), 1.38 (s, 9H), 1.08 (d, J=7.8 Hz, 3H).

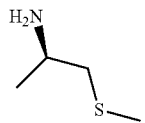

C. (R)-1-(Methylthio)propan-2-amine hydrochloride

Acetyl chloride (150 mL,) was added to a stirred solution of MeOH (600 mL) cooled with an icebath. The mixture was stirred for 30 min in an icebath, then added to (R)-tert-butyl (1-(methylthio)propan-2-yl)carbamate (78 g, 380 mmol). The mixture was stirred at rt for 2 h, (CO$_2$, (CH$_3$)$_2$C=CH$_2$ evolution) and then stripped off to a white solid: $^1$H NMR (400 MHz, DMSO-d$_6$) δ 8.22 (bs, 3H), 3.36-3.29 (m, 1H), 2.80-2.75 (m, 1H), 2.64-2.59 (m, 1H), 2.10 (s, 3H), 1.27 (d, J=6.6 Hz, 3H).

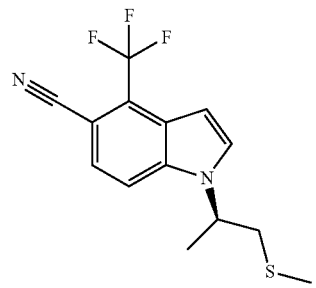 [SMILES: CSC[C@@H](C)n1ccc2c(C(F)(F)F)c(C#N)ccc21]

D. (R)-1-(1-(Methylthio)propan-2-yl)-4-(trifluoromethyl)-1H-indole-5-carbonitrile A mixture of 4-fluoro-2-(trifluoromethyl)-3-((trimethylsilyl)ethynyl)benzonitrile (Example 21D, 1.16 g, 4.07 mmol), (R)-1-(methylthio)propan-2-amine (0.599 g, 5.69 mmol) and DIEA (1.42 mL, 8.13 mmol) in DMSO (7 mL) was heated (sealed tube) at 100° C. for 50 min. Upon cooling, the reaction mixture was diluted with EtOAc (50 mL) and washed with water (30 mL). The organic phase was washed with water and brine, dried over Na$_2$SO$_4$, filtered and concentrated to give the intermediate aniline. This intermediate was dissolved in NMP (7 mL), treated with KOtBu (1 M in THF) (5.69 mL, 5.60 mmol) and heated at 50° C. The reaction was monitored by LCMS, and deemed complete after 40 min. Upon cooling, the reaction mixture was diluted with EtOAc (40 mL) and washed with water (30 mL). The organic phase was washed with more water and brine, dried over Na$_2$SO$_4$, filtered and concentrated. The residue was chromatographed over silica gel using a 5-40% EtOAc-hexane gradient to give the thioether intermediate: MS (ESI): m/z 299 (MH+).

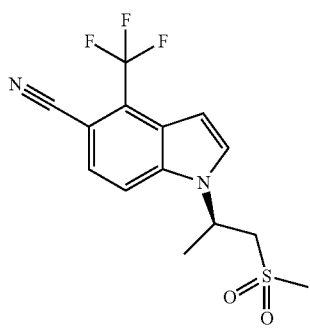 [SMILES: C[C@H](CS(C)(=O)=O)n1ccc2c(C(F)(F)F)c(C#N)ccc21]

E. (R)-1-(1-(Methylsulfonyl)propan-2-yl)-4-(trifluoromethyl)-1H-indole-5-carbonitrile To an ice-cold solution of (R)-1-(1-(methylthio)propan-2-yl)-4-(trifluoromethyl)-1H-indole-5-carbonitrile (0.560 g, 1.88 mmol) in MeOH (10 mL) was added a solution of Oxone (4.04 g, 6.57 mmol) in water (10 mL). After 50 min, the reaction mixture was diluted with water (30 mL) and extracted with EtOAc (50 mL). The organic phase was washed with brine, dried over $Na_2SO_4$, filtered and concentrated. The residue was chromatographed over silica gel using 100% $CH_2Cl_2$ to give (R)-1-(1-(methylsulfonyl)propan-2-yl)-4-(trifluoromethyl)-1H-indole-5-carbonitrile as a white foam that was crystallized from $CH_2Cl_2$/hexanes to afford a white solid (0.508 g, 79% yield): $^1$H NMR (400 MHz, DMSO-$d_6$) δ 8.17 (d, J=8.6 Hz, 1H), 8.12 (d, J=3.5 Hz, 1H), 7.81 (d, J=8.5 Hz, 1H), 6.87-6.84 (m, 1H), 5.43-5.35 (m, 1H), 4.01 (dd, J=14.8, 8.6 Hz, 1H), 3.83 (dd, J=14.8, 4.9 Hz, 1H), 2.77 (s, 3H), 1.59 (d, J=6.8 Hz, 3H); MS (ESI): m/z 331 (M+H).

Example 28

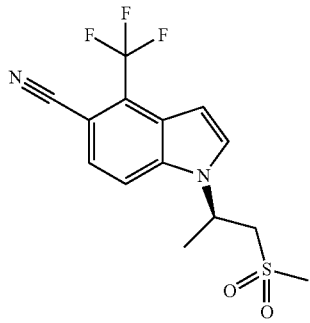 [SMILES: C[C@H](CS(C)(=O)=O)n1ccc2c(C(F)(F)F)c(C#N)ccc21]

(R)-1-(1-(Methylsulfonyl)propan-2-yl)-4-(trifluoromethyl)indoline-5-carbonitrile Synthesized in a manner similar to Example 23 using (R)-1-(1-(methylsulfonyl)propan-2-yl)-4-(trifluoromethyl)-1H-indole-5-carbonitrile (Example 27): MS (ESI): m/z 333 (M+H).

Example 29

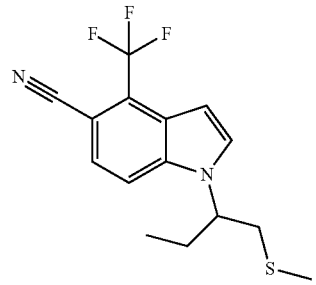 [SMILES: CCC(CSC)n1ccc2c(C(F)(F)F)c(C#N)ccc21]

1-(1-(Methylthio)butan-2-yl)-4-(trifluoromethyl)-1H-indole-5-carbonitrile

Synthesized in 3 steps, starting with methyl 2-(5-cyano-4-(trifluoromethyl)-1H-indol-1-yl)butanoate (Example 24A) using procedures similar to those described for Examples 7 and 8: MS (ESI): m/z 313 (MH+).

Example 30

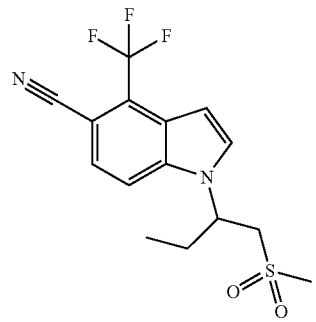 [SMILES: CCC(CS(C)(=O)=O)n1ccc2c(C(F)(F)F)c(C#N)ccc21]

1-(1-(Methylsulfonyl)butan-2-yl)-4-(trifluoromethyl)-1H-indole-5-carbonitrile

Synthesized in a manner similar to Example 9 using 1-(1-(methylthio)butan-2-yl)-4-(trifluoromethyl)-1H-indole-5-carbonitrile (Example 29): MS (ESI): m/z 345 (MH+).

Example 31

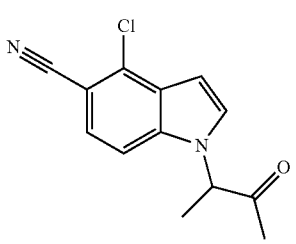 [SMILES: CC(=O)C(C)n1ccc2c(Cl)c(C#N)ccc21]

4-Chloro-1-(3-oxobutan-2-yl)-1H-indole-5-carbonitrile

Synthesized in a manner similar to Example 1 using 4-chloro-1H-indole-5-carbonitrile (see, for example, US2008139631A1) and 3-bromobutan-2-one: MS (ESI): m/z 247 (MH+).

Example 32

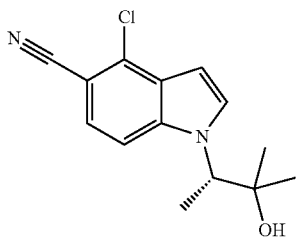 [SMILES: C[C@H](n1ccc2c(Cl)c(C#N)ccc21)C(C)(C)O]

(S)-4-Chloro-1-(3-hydroxy-3-methylbutan-2-yl)-1H-indole-5-carbonitrile

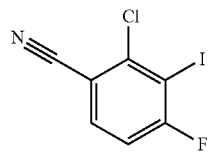 [SMILES: N#Cc1ccc(F)c(I)c1Cl]

A. 2-Chloro-4-fluoro-3-iodobenzonitrile

To a freshly-prepared solution of LDA (33.7 mmol) in anhydrous THF (30 mL) at −78° C. was added a solution of commercially available 2-chloro-4-fluorobenzonitrile (5.00 g, 32.1 mmol) in THF (10 mL), dropwise at such a rate that the internal temperature remained <−70° C. The mixture was stirred for 2 h and a solution of iodine (8.97 g, 35.4 mmol) in THF (20 mL) was added dropwise (temp <−70° C.). The mixture was stirred 30 min, removed from the cooling bath and quenched by addition of 10% $Na_2S_2O_3$. The mixture was poured into water and extracted with EtOAc (×3). Combined organics were washed (water, brine), dried over $Na_2SO_4$ and concentrated in vacuo. The residue was dissolved in a small amount of $CH_2Cl_2$ and filtered through a pad of silica (25% EtOAc/hexanes eluent). Fractions containing the major product were concentrated in vacuo and the residue was recrystallized from heptane affording 3.24 g tan solid. The mother liquor was concentrated and the residue was purified by flash chromatography (EtOAc/hexanes, gradient elution) affording 2.85 g of a pale yellow solid. Solids were combined to give 2-chloro-4-fluoro-3-iodobenzonitrile (6.09 g, 67% yield): $^1$H NMR (400 MHz, $CDCl_3$) δ 7.70 (dd, J=8.6, 5.5 Hz, 1H), 7.08 (dd, J=8.6, 6.8 Hz, 1H); MS (GCMS EI) m/z 281 ([M]+, 100%).

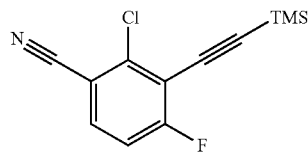 [SMILES: C[Si](C)(C)C#Cc1c(F)ccc(C#N)c1Cl]

B. 2-Chloro-4-fluoro-3-((trimethylsilyl)ethynyl)benzonitrile

A thick-walled glass pressure vessel was charged with 2-chloro-4-fluoro-3-iodobenzonitrile (2.815 g, 10.00 mmol), $Pd(PPh_3)_2Cl_2$ (0.351 g, 0.500 mmol), and CuI (0.095 g, 0.500 mmol) and sealed with a rubber septum. Anhydrous THF (25 mL) and DIPA (4.22 mL, 30.0 mmol) were added via syringe and the mixture was degassed 10 min by sparging with $N_2$ while immersed in an ultrasonic cleaning bath. To the degassed mixture was added ethynyltrimethylsilane (4.24 mL, 30.0 mmol), the vessel was resealed with a PTFE bushing, and the mixture was stirred in a heating block at 50° C. After 41 h, the mixture was cooled and poured into half-satd $NH_4Cl$. The whole was filtered through a pad of Celite and the filtrate was extracted with EtOAc (×3). Combined organics were washed (water, brine), dried over $Na_2SO_4$ and concentrated in vacuo. The residue was purified by low pressure liquid chromatography (silica gel, EtOAc/hexanes, gradient elution) affording 2-chloro-4-fluoro-3-((trimethylsilyl)ethynyl)benzonitrile (2.29 g, 91% yield) as a pale yellow solid: $^1$H NMR (400 MHz, $CDCl_3$) δ 7.60 (dd, J=8.7, 5.4 Hz, 1H), 7.12 (dd, J=8.7, 7.9 Hz, 1H), 0.30 (s, 9H); MS (GCMS EI) m/z 251 ([M]+, 14%), 236 ([M-$CH_3$]+, 100%).

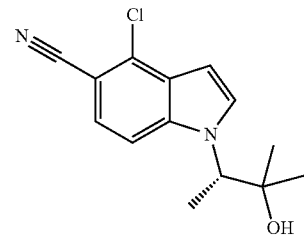 [SMILES: C[C@H](n1ccc2c(Cl)c(C#N)ccc21)C(C)(C)O]

C. (S)-4-Chloro-1-(3-hydroxy-3-methylbutan-2-yl)-1H-indole-5-carbonitrile

A mixture of 2-chloro-4-fluoro-3-((trimethylsilyl)ethynyl)benzonitrile, (0.229 g, 0.91 mmol), (S)-3-amino-2-methylbutan-2-ol (Example 21E) (0.113 g, 1.092 mmol), and $K_2CO_3$ (0.252 g, 1.820 mmol) in anhyd NMP (3 mL) was stirred in a heating block at 60° C. under $N_2$ for 2 h. CuI (0.017 g; 0.091 mmol) was added and the mixture was subjected to microwave heating (140° C.) for 30 min. The reaction mixture was poured into EtOAc/water and the whole was filtered through a pad of Celite. Layers of the filtrate were separated and the aqueous layer was extracted with EtOAc (×2). Combined organics were filtered (Whatman #2), washed (water, brine), dried over $Na_2SO_4$ and concentrated in vacuo. The residue was purified by low pressure liquid chromatography (silica gel, EtOAc/hexanes, gradient elution) affording (S)-4-chloro-1-(3-hydroxy-3-methylbutan-2-yl)-1H-indole-5-carbonitrile (0.148 g, 62% yield) as a pale yellow solid: $^1$H NMR (400 MHz, CDCl$_3$) δ 7.50 (d, 1H), 7.42-7.39 (m, 1H), 7.39-7.34 (m, 1H), 6.74 (d, J=3.3 Hz, 1H), 4.41 (q, J=7.0 Hz, 1H), 1.60 (d, J=7.1 Hz, 3H), 1.41 (s, 1H), 1.33 (s, 3H), 1.09 (s, 3H); MS (LCMS ES+) m/z 263 ([M+H]$^+$, 88%), 304 ({[M+H]+MeCN}$^+$, 100%).

Example 33

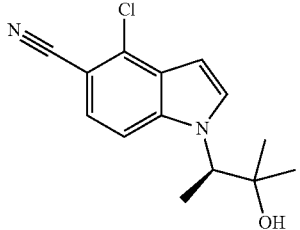 [SMILES: C[C@@H](n1ccc2c(Cl)c(C#N)ccc21)C(C)(C)O]

(R)-4-Chloro-1-(3-hydroxy-3-methylbutan-2-yl)-1H-indole-5-carbonitrile

To a solution of (R)-3-amino-2-methylbutan-2-ol (made in a manner similar to Example 21G using commercially available (S)-methyl 2-aminopropanoate, hydrochloride) (0.1084 g, 1.051 mmol) and 2-chloro-4-fluoro-3-((trimethylsilyl)ethynyl)benzonitrile (Example 32B) (0.212 g, 0.841 mmol) in anhyd NMP (4 mL) at rt was added DBU (0.475 mL, 3.15 mmol), dropwise via syringe. The reaction vial was sealed with a crimp top and subjected to microwave heating (140° C.) for 40 min. Upon cooling the mixture was poured into satd NaHCO$_3$ and extracted with EtOAc (×3). Combined organics were washed (water, brine), dried over Na$_2$SO$_4$ and concentrated in vacuo. The residue was purified by preparative HPLC (C18 stationary phase, MeCN/water gradient with 0.1% TFA additive) affording (R)-4-chloro-1-(3-hydroxy-3-methylbutan-2-yl)-1H-indole-5-carbonitrile (0.0188 g, 7% yield) as a tan film: $^1$H NMR (400 MHz, CDCl$_3$) δ 7.50 (d, J=3.4 Hz, 1H), 7.41 (d, J=8.6 Hz, 1H), 7.37 (d, J=8.6 Hz, 1H), 6.74 (d, J=3.3 Hz, 1H), 4.41 (q, J=7.0 Hz, 1H), 1.60 (d, J=7.0 Hz, 3H), 1.33 (s, 3H), 1.10 (s, 3H); MS (LCMS ES+) m/z 263 ([M+H]$^+$, 52%), 304 ({[M+H]+MeCN}$^+$, 100%).

Example 34

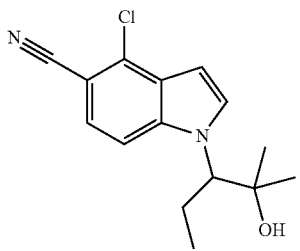 [SMILES: CCC(n1ccc2c(Cl)c(C#N)ccc21)C(C)(C)O]

4-Chloro-1-(2-hydroxy-2-methylpentan-3-yl)-1H-indole-5-carbonitrile

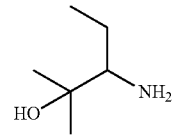

A. 3-Amino-2-methylpentan-2-ol

Synthesized in a manner similar to Example 21G starting with commercially available methyl 2-aminobutanoate hydrochloride: $^1$H NMR (400 MHz, CDCl$_3$) δ 2.37-2.35 (m, 1H), 1.69-1.64 (m, 2H), 1.19 (s, 3H), 1.05 (s, 3H), 1.01-0.98 (m, 3H).

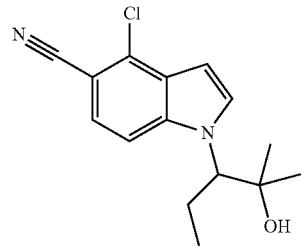 [SMILES: CCC(n1ccc2c(Cl)c(C#N)ccc21)C(C)(C)O]

B. 4-Chloro-1-(2-hydroxy-2-methylpentan-3-yl)-1H-indole-5-carbonitrile

A mixture of 2-chloro-4-fluoro-3-((trimethylsilyl)ethynyl)benzonitrile (Example 32B) (0.163 g, 0.647 mmol), 3-amino-2-methylpentan-2-ol (0.091 g, 0.776 mmol), and K$_2$CO$_3$ (0.179 g, 1.294 mmol) in anhyd NMP (3 mL) was stirred in a heating block at 60° C. under N$_2$. After 18 h, the mixture was subjected to microwave heating (140° C.) for 15 min. Upon cooling the mixture was poured into water and extracted with EtOAc (×3). Combined organics were washed (water, brine), dried over Na$_2$SO$_4$ and concentrated in vacuo. The residue was purified by low pressure liquid chromatography (silica gel, EtOAc/hexanes, gradient elution) affording 4-chloro-1-(2-hydroxy-2-methylpentan-3-yl)-1H-indole-5-carbonitrile (0.0761 g, 43% yield) as a yellow gum. $^1$H NMR (400 MHz, CDCl$_3$) δ 7.48 (d, J=2.2 Hz, 1H), 7.42 (d, J=8.6 Hz, 1H), 7.35 (d, J=8.7 Hz, 1H), 6.77 (d, J=3.3 Hz, 1H), 4.07 (dd, J=11.6, 3.6 Hz, 1H), 2.09 (m, J=3.6 Hz, 2H), 1.44 (s, 1H), 1.35 (s, 3H), 1.08 (s, 3H), 0.65 (t, J=7.3 Hz, 3H); MS (LCMS ES+) m/z 277 ([M+H]$^+$, 70%), 318 ({[M+H]+MeCN}$^+$, 100%).

Example 35

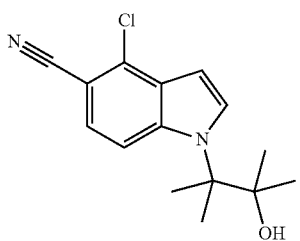

4-Chloro-1-(3-hydroxy-2,3-dimethylbutan-2-yl)-1H-indole-5-carbonitrile

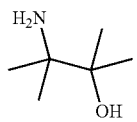

A. 3-Amino-2,3-dimethylbutan-2-ol

Synthesized in a manner similar to Example 21G starting with commercially available methyl 2-amino-2-methylpropanoate: $^1$H NMR (400 MHz, CDCl$_3$) δ 1.18 (s, 6H), 1.16 (s, 6H).

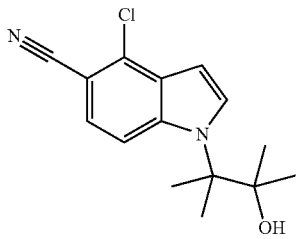 [SMILES: CC(C)(O)C(C)(C)n1ccc2c(Cl)c(C#N)ccc21]

B. 4-Chloro-1-(3-hydroxy-2,3-dimethylbutan-2-yl)-1H-indole-5-carbonitrile

An oven-dried vial was charged with 3-amino-2,3-dimethylbutan-2-ol (0.063 g, 0.539 mmol), 2-chloro-4-fluoro-3-((trimethylsilyl)ethynyl)benzonitrile (Example 32B) (0.113 g, 0.449 mmol), and K$_2$CO$_3$ (0.137 g, 0.988 mmol) and sealed with a rubber septum. Anhyd NMP (3 mL) was added via syringe and the mixture was stirred in a heating block at 60° C. under N$_2$. After 1 h, the vial was sealed with a PTFE-faced crimp top and subjected to microwave heating; 1 h at 140° C. followed by 45 min at 160° C. (with air cooling). The mixture was poured into water/EtOAc and the whole was filtered through a pad of Celite. Layers of the filtrate were separated and the aqueous layer was extracted with EtOAc (×2). Combined organics were washed (water, brine), dried over Na$_2$SO$_4$ and concentrated in vacuo. The residue was purified by preparative HPLC (C18 stationary phase, MeCN/water gradient with 0.1% TFA additive) affording 4-chloro-1-(3-hydroxy-2,3-dimethylbutan-2-yl)-1H-indole-5-carbonitrile (0.0066 g, 5% yield) as a tan solid (ca. 85% purity): $^1$H NMR (400 MHz, CDCl$_3$) δ 7.84 (d, J=9.0 Hz, 1H), 7.49 (d, J=3.5 Hz, 1H), 7.32 (d, J=8.9 Hz, 1H), 6.71 (d, J=3.4 Hz, 1H), 1.87 (s, 6H), 1.20 (s, 6H); MS (LCMS ES+) m/z 277 ([M+H]$^+$, 65%), 318 ({[M+H]+MeCN}+, 100%).

Example 36

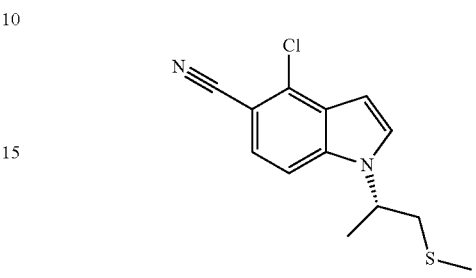

(S)-4-Chloro-1-(1-(methylthio)propan-2-yl)-1H-indole-5-carbonitrile

A mixture of 2-chloro-4-fluoro-3-((trimethylsilyl)ethynyl)benzonitrile (Example 32B) (0.120 g, 0.477 mmol), (S)-1-(methylthio)propan-2-amine (0.075 g, 0.715 mmol) (prepared essentially as described in US2005182275A1) and DIEA (0.166 mL, 0.953 mmol) in DMSO (2 mL) was heated (sealed tube) at 100° C. for 45 min. Upon cooling, the reaction mixture was diluted with EtOAc (25 mL) and washed with water (20 mL). The organic phase was washed with water and brine, dried over Na$_2$SO$_4$, filtered and concentrated to give the intermediate (S)-2-chloro-3-ethynyl-4-((1-(methylthio)propan-2-yl)amino)benzonitrile. This intermediate was dissolved in NMP (2 mL), treated with KOtBu (1 M in THF) (1.430 mL, 1.430 mmol) and heated at 60° C. The reaction was monitored by LCMS, and after 45 min, additional KOtBu (1 M in THF) (1.430 mL, 1.430 mmol) was added and heating continued for another 1 h. Upon cooling, the reaction mixture was diluted with EtOAc (25 mL) and washed with water (20 mL). The organic phase was washed with water and brine, dried over Na$_2$SO$_4$, filtered and concentrated. The residue was chromatographed over silica gel using a 5-30% EtOAc-hexane gradient to give (S)-4-chloro-1-(1-(methylthio)propan-2-yl)-1H-indole-5-carbonitrile (0.056 g, 42% yield): MS (ESI): m/z 265 (M+H).

Example 37

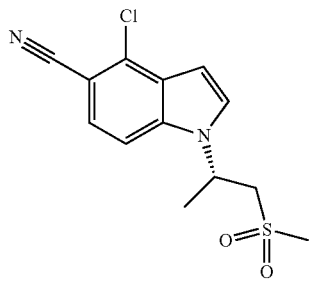 [SMILES: C[C@@H](CS(C)(=O)=O)n1ccc2c(Cl)c(C#N)ccc21]

(S)-4-Chloro-1-(1-(methylsulfonyl)propan-2-yl)-1H-indole-5-carbonitrile

Synthesized in a manner similar to Example 9 using (S)-4-chloro-1-(1-(methylthio)propan-2-yl)-1H-indole-5-carbonitrile (Example 36): MS (ESI): m/z 297 (MH+).

Example 38

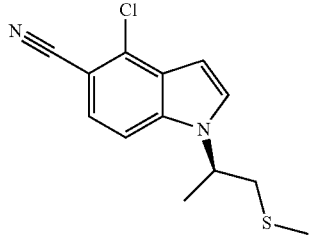 [SMILES: CSC[C@@H](C)n1ccc2c(Cl)c(C#N)ccc21]

(R)-4-Chloro-1-(1-(methylthio)propan-2-yl)-1H-indole-5-carbonitrile

Synthesized in a manner similar to Example 36 using 2-chloro-4-fluoro-3-((trimethylsilyl)ethynyl)benzonitrile (Example 32B) and (R)-1-(methylthio)propan-2-amine (Example 27C): MS (ESI): m/z 265 (M+H).

Example 39

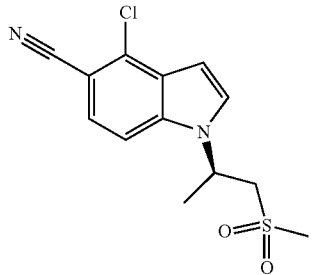 [SMILES: C[C@H](CS(C)(=O)=O)n1ccc2c(Cl)c(C#N)ccc21]

(R)-4-Chloro-1-(1-(methylsulfonyl)propan-2-yl)-1H-indole-5-carbonitrile

Synthesized in a manner similar to Example 9 using (R)-4-chloro-1-(1-(methylthio)propan-2-yl)-1H-indole-5-carbonitrile (Example 38): MS (ESI): m/z 297 (MH+).

Example 40

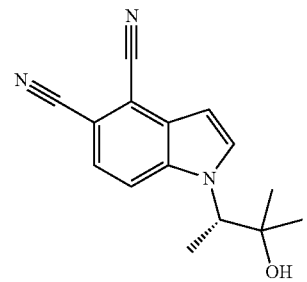 [SMILES: C[C@H](n1ccc2c(C#N)c(C#N)ccc21)C(C)(C)O]

(S)-1-(3-Hydroxy-3-methylbutan-2-yl)-1H-indole-4,5-dicarbonitrile

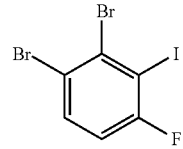

A. 1,2-Dibromo-4-fluoro-3-iodobenzene

To a solution of freshly-prepared LDA (33.9 mmol) in anhyd THF (100 mL) at −78° C. was added a solution of 1,2-dibromo-4-fluorobenzene (4 mL, 32.3 mmol) in THF (8 mL), dropwise at such a rate that the internal temperature remained <−70° C. The mixture was stirred 30 min and iodine (9.02 g, 35.5 mmol) was added in one portion. The mixture was stirred 30 min, quenched by addition of 10% $Na_2S_2O_3$, and removed from the cooling bath. Upon warming the mixture was poured into water and extracted with EtOAc (×3). Combined organics were washed (water, brine), dried over $Na_2SO_4$ and concentrated in vacuo. The residue was eluted from a pad of silica (hexanes→2% EtOAc/hexanes) and recrystallized from MeOH-water affording 1,2-dibromo-4-fluoro-3-iodobenzene (8.59 g, 70% yield) as a white solid: $^1$H NMR (400 MHz, CDCl$_3$) δ 7.64 (dd, J=8.8, 5.5 Hz, 1H), 6.93 (dd, J=8.8, 7.0 Hz, 1H); MS (GCMS EI) m/z 378 ([M]$^+$, Br isotopes, 56%), 380 ([M]+, Br isotopes, 100%), 382 ([M]+, Br isotopes, 51%).

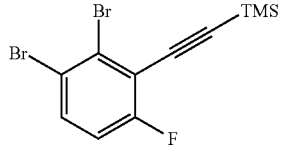

B. ((2,3-Dibromo-6-fluorophenyl)ethynyl)trimethylsilane

A thick-walled glass vessel was charged with 1,2-dibromo-4-fluoro-3-iodobenzene (8.31 g, 21.88 mmol), Pd(PPh$_3$)$_2$Cl$_2$ (0.768 g, 1.094 mmol), and CuI (0.292 g, 1.532 mmol) and sealed with a rubber septum. Anhyd THF (30 mL) and DIPA (30.8 mL, 219 mmol) were added via syringe and the mixture was degassed 10 min by sparging with N$_2$ while immersed in an ultrasonic bath. Ethynyltrimethylsilane (3.40 mL, 24.07 mmol) was added via syringe and the septum was replaced with a PTFE bushing. The mixture was stirred in an oil bath at 40° C. After 40 h, the mixture was cooled, diluted with EtOAc and filtered through a pad of Celite. The filtrate was washed (satd NH$_4$Cl×2, water, brine), dried over Na$_2$SO$_4$ and concentrated in vacuo. The residue was purified by low pressure liquid chromatography (silica gel, EtOAc/hexanes, gradient elution) affording ((2,3-dibromo-6-fluorophenyl)ethynyl)trimethylsilane (6.08 g, 17.37 mmol, 79% yield) as a yellow oil: $^1$H NMR (400 MHz, CDCl$_3$) δ 7.53 (dd, J=8.9, 5.4 Hz, 1H), 6.95 (dd, J=8.9, 8.1 Hz, 1H), 0.29 (s, 9H); MS (GCMS EI) m/z 348 ([M]$^+$, Br isotopes, 18%), 350 ([M]$^+$, Br isotopes, 34%), 352

([M]+, Br isotopes, 18%), 333 ([M-CH₃]+, Br isotopes, 56%), 335 ([M-CH₃]+, Br isotopes, 100%), 337 ([M-CH3]+, Br isotopes, 54%).

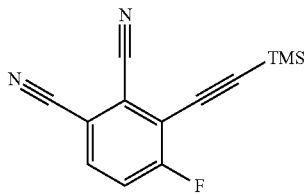 [SMILES: C[Si](C)(C)C#Cc1c(F)ccc(C#N)c1C#N]

C. 4-Fluoro-3-((trimethylsilyl)ethynyl)phthalonitrile

An oven-dried flask was charged with ((2,3-dibromo-6-fluorophenyl)ethynyl)trimethylsilane, (6.08 g, 17.37 mmol), Zn(CN)₂ (2.039 g, 17.37 mmol), Pd₂(dba)₃ (0.477 g, 0.521 mmol), and dppf (0.481 g, 0.868 mmol) and sealed with a rubber septum. Anhyd DMAC (25 mL) and PMHS (0.344 mL, 17.37 mmol) were added via syringe and the mixture was degassed 10 min by sparging with N₂ while immersed in an ultrasonic cleaning bath. The mixture was stirred in an oil bath at 100° C. under nitrogen. After 26 h the mixture was cooled, poured into satd NaHCO₃ and extracted with EtOAc (×3). Combined organics were washed (water, brine), dried over Na₂SO₄ and concentrated in vacuo. The residue was purified by low pressure liquid chromatography (silica gel, EtOAc/hexanes, gradient elution) affording 4-fluoro-3-((trimethylsilyl)ethynyl)phthalonitrile (2.98 g, 71% yield) as a tan solid: ¹H NMR (400 MHz, CDCl₃) δ 7.72 (dd, J=8.7, 4.7 Hz, 1H), 7.43 (dd, J=8.6, 8.0 Hz, 1H), 0.32 (s, 9H); MS (GCMS EI) m/z 242 ([M]+, 7%), 227 ([M-CH₃]+, 100%).

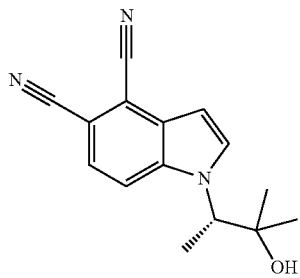 [SMILES: C[C@H](n1ccc2c(C#N)c(C#N)ccc21)C(C)(C)O]

D. (S)-1-(3-Hydroxy-3-methyl butan-2-yl)-1H-indole-4,5-dicarbonitrile

An oven-dried vial was charged with (S)-3-amino-2-methylbutan-2-ol (Example 21G) (0.064 g, 0.622 mmol), 4-fluoro-3-((trimethylsilyl)ethynyl)phthalonitrile (0.126 g, 0.518 mmol), and K₂CO₃ (0.143 g, 1.036 mmol) and sealed with a rubber septum. Anhyd NMP (3 mL) was added via syringe and the mixture was stirred in a heating block at 60° C. under N₂. After 30 min, the vial was sealed with a PTFE-faced crimp top and the mixture was subjected to microwave heating (140° C.) for 15 min. The mixture was poured into water and extracted with EtOAc (×3). Combined organics were washed (water, brine), dried over Na₂SO₄ and concentrated in vacuo. The residue was purified by low pressure liquid chromatography (silica gel, EtOAc/hexanes, gradient elution) affording (S)-1-(3-hydroxy-3-methylbutan-2-yl)-1H-indole-4,5-dicarbonitrile (0.0659 g, 50% yield) as a tan solid: ¹H NMR (400 MHz, CDCl₃) δ 7.73 (d, J=8.7, Hz, 1H), 7.69 (d, J=3.3 Hz, 1H), 7.51 (d, J=8.7 Hz, 1H), 6.84 (d, J=3.2 Hz, 1H), 4.47 (q, J=7.0 Hz, 1H), 1.63 (d, J=7.0 Hz, 3H), 1.53 (s, 1H), 1.34 (s, 3H), 1.11 (s, 3H).

Example 41

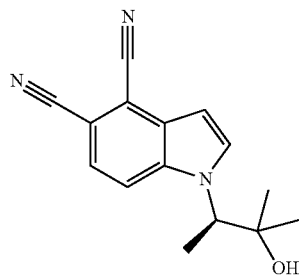 [SMILES: C[C@@H](n1ccc2c(C#N)c(C#N)ccc21)C(C)(C)O]

(R)-1-(3-Hydroxy-3-methylbutan-2-yl)-1H-indole-4,5-dicarbonitrile

An oven-dried vial was charged with (R)-3-amino-2-methylbutan-2-ol (made in a manner similar to Example 21G using commercially available (S)-methyl 2-aminopropanoate, hydrochloride) (0.072 g, 0.696 mmol), 4-fluoro-3-((trimethylsilyl)ethynyl)phthalonitrile (Example 40C) (0.141 g, 0.58 mmol), anhyd NMP (3.5 mL) and DIEA (0.304 mL, 1.740 mmol), and the vial was sealed with a crimp top. The mixture was subjected to microwave heating (140° C.) for 20 min. Upon cooling the mixture was poured into satd NaHCO₃ and extracted with EtOAc (×3). Combined organics were washed (water, brine), dried over Na₂SO₄ and concentrated in vacuo. The residue was purified by low pressure liquid chromatography (silica gel, EtOAc/hexanes, gradient elution) affording 0.0572 g (0.226 mmol) of the aniline intermediate. The aniline was dissolved in anhyd NMP (2 mL) and a solution of KOtBu in THF (0.250 mL, 0.25 mmol) was added via syringe. The mixture was stirred overnight at rt under N₂. After ca. 24 h, the mixture was poured into satd NaHCO₃ and extracted with EtOAc (×3). Combined organics were washed (water, brine), dried over Na₂SO₄ and concentrated in vacuo. The residue was purified by low pressure liquid chromatography (silica gel, EtOAc/hexanes, gradient elution) affording (R)-1-(3-hydroxy-3-methylbutan-2-yl)-1H-indole-4,5-dicarbonitrile (0.0285 g, 19% yield) as a colorless film: ¹H NMR (400 MHz, CDCl₃) δ 7.73 (d, J=8.7, Hz, 1H), 7.69 (d, J=3.4 Hz, 1H), 7.51 (d, J=8.6 Hz, 1H), 6.84 (d, J=3.4 Hz, 1H), 4.46 (q, J=7.1 Hz, 1H), 1.63 (d, J=7.0 Hz, 3H), 1.48 (s, 1H), 1.34 (s, 3H), 1.11 (s, 3H).

Example 42

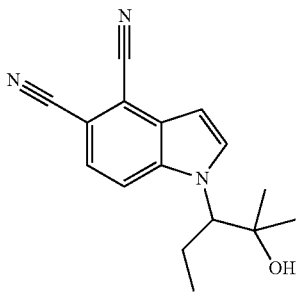 [SMILES: CCC(n1ccc2c(C#N)c(C#N)ccc21)C(C)(C)O]

1-(2-Hydroxy-2-methylpentan-3-yl)-1H-indole-4,5-dicarbonitrile

An oven-dried 20 mL microwave vial was charged with 3-amino-2-methylpentan-2-ol (Example 34A) (0.0705 g, 0.602 mmol), 4-fluoro-3-((trimethylsilyl)ethynyl)phthalonitrile (Example 40C) (0.146 g, 0.602 mmol), and K$_2$CO$_3$ (0.100 g, 0.722 mmol). Anhyd NMP (3 mL) was added via syringe and the vial was sealed with a PTFE-faced crimp top. The mixture was subjected to microwave heating (140° C.) for 35 min. The mixture was cooled, poured into satd NaHCO$_3$, layered with EtOAc and the whole was filtered (Whatman #2). Layers were separated and the aqueous layer was extracted with EtOAc (×2). Combined organics were washed (water, brine), dried over Na$_2$SO$_4$ and concentrated in vacuo. The residue was purified by low pressure liquid chromatography (silica gel, EtOAc/hexanes, gradient elution). Fractions containing the desired product were decolorized with activated carbon affording 1-(2-hydroxy-2-methylpentan-3-yl)-1H-indole-4,5-dicarbonitrile (0.0285 g, 18% yield) as an amber film: $^1$H NMR (400 MHz, CDCl$_3$) δ 7.75-7.61 (m, 2H), 7.53 (d, J=8.6 Hz, 1H), 6.88 (d, J=3.3 Hz, 1H), 4.16-4.07 (m, 1H), 2.20-2.01 (m, 2H), 1.37 (s, 3H), 1.08 (s, 3H), 0.65 (t, J=7.3 Hz, 3H); MS (LCMS ES+) m/z 268 ([M+H]$^+$, 26%), 285 (100%), 309 ({[M+H]+MeCN}+, 78%).

Example 43

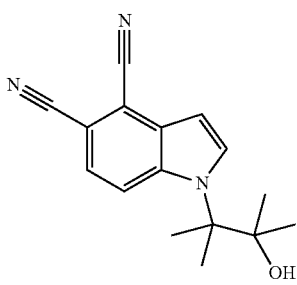 [SMILES: CC(C)(O)C(C)(C)n1ccc2c(C#N)c(C#N)ccc21]

1-(3-Hydroxy-2,3-dimethylbutan-2-yl)-1H-indole-4,5-dicarbonitrile

An oven-dried vial was charged with 3-amino-2,3-dimethylbutan-2-ol (Example 35A) (0.063 g, 0.540 mmol), and 4-fluoro-3-((trimethylsilyl)ethynyl)phthalonitrile (Example 40C) (0.109 g, 0.45 mmol) and sealed with a rubber septum. DIEA (0.157 mL, 0.900 mmol) and anhyd DMSO (2 mL) were added via syringe and the mixture was stirred at rt under N$_2$. After 18 h, the temperature was increased to 60° C. and stirring continued an additional 30 h. Upon cooling the mixture was poured into water and extracted with EtOAc (×3). Combined organics were washed (water, brine), dried over Na$_2$SO$_4$ and concentrated in vacuo to a dark, oily residue. An oven-dried vial was charged with the residue, followed by CuI (0.043 g, 0.225 mmol) and sealed with a rubber septum. Anhyd DMF (3 mL) was added via syringe and the septum was replaced with a PTFE-faced crimp top. The mixture was subjected to microwave heating (140° C.) for 20 min. The mixture was poured into satd NH$_4$Cl and extracted with EtOAc (×3). Combined organics were washed (water, brine), dried over Na$_2$SO$_4$ and concentrated in vacuo. The residue was purified by low pressure liquid chromatography (silica gel, EtOAc/hexanes, gradient elution) followed by preparative HPLC (C18 stationary phase, MeCN/water gradient with 0.1% TFA additive) affording 1-(3-hydroxy-2,3-dimethylbutan-2-yl)-1H-indole-4,5-dicarbonitrile (0.0093 g, 8% yield) as a colorless solid: $^1$H NMR (400 MHz, CDCl$_3$) δ 8.21 (dd, J=9.0, 0.8 Hz, 1H), 7.65 (d, J=3.5 Hz, 1H), 7.42 (d, J=9.0 Hz, 1H), 6.81 (dd, J=3.5, 0.8 Hz, 1H), 1.88 (s, 6H), 1.21 (s, 6H); MS (LCMS ES+) m/z 268 ([M+H]$^+$, 29%), 309 ({[M+H]+MeCN}$^+$, 100%).

Example 44

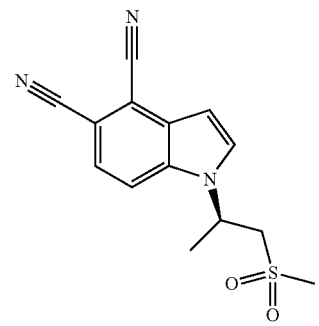 [SMILES: C[C@H](CS(C)(=O)=O)n1ccc2c(C#N)c(C#N)ccc21]

(R)-1-(1-(Methylsulfonyl)propan-2-yl)-1H-indole-4,5-dicarbonitrile

A mixture of (R)-4-chloro-1-(1-(methylsulfonyl)propan-2-yl)-1H-indole-5-carbonitrile (Example 39) (0.043 g, 0.145 mmol), Zn(CN)$_2$ (0.034 g, 0.290 mmol) and Pd(PPh$_3$)$_4$ (0.0335 g, 0.029 mmol) in DMF (3 mL) was sparged with N$_2$ for 5 minutes, and then heated at 120° C. in a sealed tube for 4 h. The reaction was monitored by LCMS, and additional zinc cyanide and tetrakis(triphenylphosphine)palladium(0) was added accordingly. After about 50% conversion, the reaction mixture was diluted with EtOAc (20 mL) and washed with water (15 mL). The organic phase was washed with brine. The combined aqueous phases were extracted with EtOAc (1×20 mL). The organic phases were combined, dried over Na$_2$SO$_4$, filtered and concentrated. The residue was purified by preparative HPLC (Phenomenex Luna column; gradient: 10-100% MeCN-water with 0.1% TFA). The fractions with product were combined and concentrated down to the aqueous phase, which was partitioned between EtOAc (20 ml) and aq. saturated Na$_2$CO$_3$ solution (20 mL).

The organic phase was washed with brine, dried over Na₂SO₄, filtered, and concentrated. The product was subsequently crystallized from CH₂Cl₂-hexanes to give (R)-4-chloro-1-(1-(methylsulfonyl)propan-2-yl)-1H-indole-5-carbonitrile as a white solid (0.015 g, 33% yield): MS (ESI): m/z 288 (M+H).

Example 45

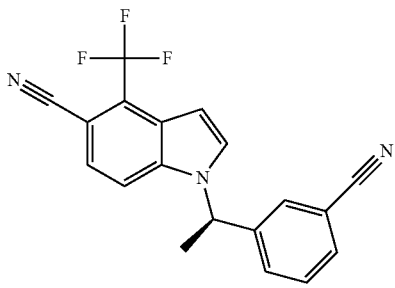 [SMILES: C[C@H](c1cccc(C#N)c1)n1ccc2c(C(F)(F)F)c(C#N)ccc21]

(R)-1-(1-(3-Cyanophenyl)ethyl)-4-(trifluoromethyl)-1H-indole-5-carbonitrile

An oven-dried vial was charged with 4-fluoro-2-(trifluoromethyl)-3-((trimethylsilyl)ethynyl)benzonitrile (Example 21D) (0.173 g, 0.606 mmol), commercially available (R)-3-(1-aminoethyl)benzonitrile (0.098 g, 0.667 mmol) and K₂CO₃ (0.092 g, 0.667 mmol) and sealed with a rubber septum. Anhyd NMP (3 mL) was added via syringe and the mixture was stirred in a heating block at 60° C. under N₂ for 17 h. The mixture was cooled, poured into satd NaHCO₃ and extracted with EtOAc (×3). Combined organics were washed (water, brine), dried over Na₂SO₄ and concentrated in vacuo. The residue was purified by low pressure liquid chromatography (silica gel, EtOAc/hexanes, gradient elution) affording (R)-1-(1-(3-cyanophenyl)ethyl)-4-(trifluoromethyl)-1H-indole-5-carbonitrile (0.0845 g, 41% yield) as a pale yellow gum which solidified upon trituration with Et₂O/hexanes: ¹H NMR (400 MHz, CDCl₃) δ 7.62 (d, J=7.6 Hz, 1H), 7.57 (d, J=4.6 Hz, 1H), 7.53 (d, J=8.5 Hz, 1H), 7.47 (t, J=7.8 Hz, 1H), 7.42 (s, 1H), 7.39 (d, J=8.6 Hz, 1H), 7.29 (d, J=6.7 Hz, 1H, overlapping with solvent), 6.96 (m, 1H), 5.76 (q, J=7.0 Hz, 1H), 2.01 (d, J=7.1 Hz, 3H); MS (LCMS ES+) m/z 340 ([M+H]⁺, 86%), 381 ({[M+H]+MeCN}⁺, 100%).

Example 46

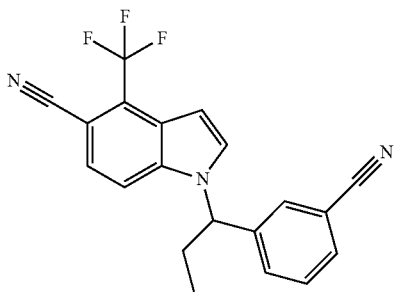 [SMILES: CCC(c1cccc(C#N)c1)n1ccc2c(C(F)(F)F)c(C#N)ccc21]

1-(1-3-Cyanophenyl)propyl)-4-(trifluoromethyl)-1H-indole-5-carbonitrile

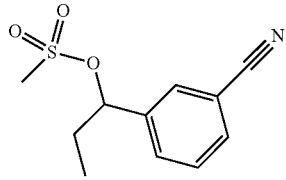 [SMILES: CCC(OS(C)(=O)=O)c1cccc(C#N)c1]

A. 1-(3-Cyanophenyl)propyl methanesulfonate

A mixture of 3-(1-hydroxypropyl)benzonitrile (0.273 g, 1.694 mmol; ref. Synlett (2002), (11), 1922-1924), Et₃N (0.354 mL, 2.54 mmol) and MsCl (0.198 mL, 2.54 mmol) in CH₂Cl₂ (5 mL) was stirred at rt. After 90 min, an additional 0.75 eq each of Et₃N and MsCl were added. After 1 h, the reaction mixture was concentrated to dryness, and the residue was partitioned between EtOAc (20 mL) and 0.1N HCl (20 mL). The organic phase was washed with water and brine, dried over Na₂SO₄, filtered and concentrated. The residue was chromatographed over silica gel using a 5-30% EtOAc-hexane gradient to give 1-(3-cyanophenyl)propyl methanesulfonate (0.289 g, 68% yield) (the product is somewhat unstable, and it needs to be used shortly thereafter or stored at low temperatures).

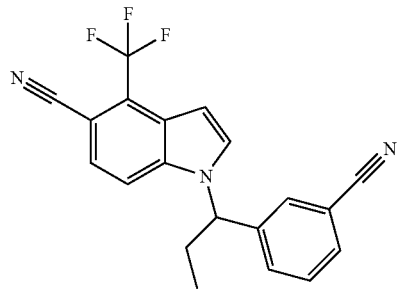 [SMILES: CCC(c1cccc(C#N)c1)n1ccc2c(C(F)(F)F)c(C#N)ccc21]

B. 1-(1-(3-Cyanophenyl)propyl)-4-(trifluoromethyl)-1H-indole-5-carbonitrile

To a suspension of 4-(trifluoromethyl)-1H-indole-5-carbonitrile (0.030 g, 0.143 mmol) in THF (5 mL) was added KOtBu (1M in THF) (0.157 mL, 0.157 mmol). After stirring at rt for a couple of min, a solution of 1-(3-cyanophenyl)propyl methanesulfonate (0.0512 g, 0.214 mmol) in THF (1 mL) was added, and the mixture was heated at 80° C. in a sealed tube. The reaction was monitored by LCMS. After ~30 min, additional 1-(3-cyanophenyl)propyl methanesulfonate (0.0342 g, 0.143 mmol) in THF (1 mL) was added, and the mixture was heated at 80° C. for another 30 min. Upon cooling, the reaction mixture was diluted with EtOAc (20 mL) and washed with water (20 mL). The organic phase was washed with brine, dried over Na₂SO₄, filtered and concentrated. The residue was chromatographed over silica gel using 0-25% EtOAc-hexane gradient. The material was further purified by preparative HPLC (Phenomenex Luna column; gradient: 10-100% MeCN-water with 0.1% TFA). The fractions with product were combined and concentrated down to the aqueous phase, which was then partitioned between EtOAc (25 mL) and saturated aq. NaHCO₃ solution (20 mL). The organic phase was washed with brine, dried over Na₂SO₄, filtered and concentrated to give 1-(1-(3-cyanophenyl)propyl)-4-(trifluoromethyl)-1H-indole-5-carbonitrile (0.014 g, 26% yield): MS (ESI): m/z 354 (M+H).

Example 47

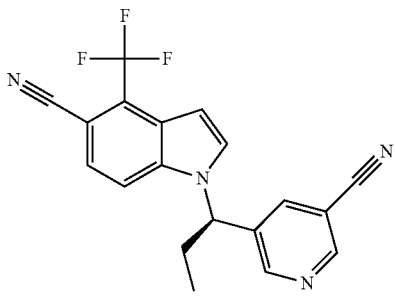 [SMILES: CC[C@H](c1cncc(C#N)c1)n1ccc2c(C(F)(F)F)c(C#N)ccc21]

(R)-1-(1-(5-Cyanopyridin-3-yl)propyl)-4-(trifluoromethyl)-1H-indole-5-carbonitrile An oven-dried vial was charged with 4-fluoro-2-(trifluoromethyl)-3-((trimethylsilyl)ethynyl)benzonitrile (Example 21D), (0.171 g, 0.598 mmol), commercially available (R)-5-(1-aminopropyl)nicotinonitrile (0.106 g, 0.658 mmol) and K₂CO₃ (0.091 g, 0.658 mmol) and sealed with a rubber septum. Anhydrous NMP (3 mL) was added via syringe and the mixture was stirred in a heating block at 60° C. under N₂. After 22 h the mixture was cooled, poured into satd NaHCO₃ and extracted with EtOAc (×3). Combined organics were washed (water, brine), dried over Na₂SO₄ and concentrated in vacuo. The residue was purified by low pressure liquid chromatography (silica gel, EtOAc/hexanes, gradient elution) affording (R)-1-(1-(5-cyanopyridin-3-yl)propyl)-4-(trifluoromethyl)-1H-indole-5-carbonitrile (0.0758 g, 36% yield) as a tan gum: ¹H NMR (400 MHz, CDCl₃) δ 8.82 (s, 1H), 8.69 (br. s., 1H), 7.64 (br. s., 1H), 7.60-7.43 (m, 3H), 7.00 (br. s., 1H), 5.49 (t, J=7.5 Hz, 1H), 2.42 (sxt, J=7.1 Hz, 2H), 1.04 (t, J=7.1 Hz, 3H); MS (LCMS ES+) m/z 355 ([M+H]⁺, 62%), 396 ({[M+H]+MeCN}⁺, 100%).

Example 48

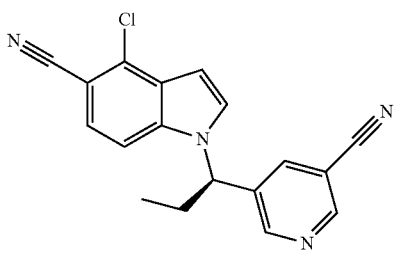 [SMILES: CC[C@H](c1cncc(C#N)c1)n1ccc2c(Cl)c(C#N)ccc21]

(R)-4-Chloro-1-(1-(5-cyanopyridin-3-yl)propyl)-1H-indole-5-carbonitrile

An oven-dried vial was charged with commercially available (R)-5-(1-aminopropyl)nicotinonitrile (0.165 g, 1.023 mmol), 2-chloro-4-fluoro-3-((trimethylsilyl)ethynyl)benzonitrile (Example 32B) (0.234 g, 0.93 mmol), and K₂CO₃ (0.141 g, 1.023 mmol) and sealed with a rubber septum. Anhyd NMP (3 mL) was added via syringe and the mixture was stirred in a heating block at 60° C. under N₂. After 18 h, the septum was replaced with a PTFE-faced crimp top and the mixture was subjected to microwave heating (140° C.) for 15 min. Upon cooling the mixture was poured into satd NaHCO₃ and extracted with EtOAc (×3). Combined organics were washed (water, brine), the combined washes were filtered (Whatman #2) and re-extracted with EtOAc (×1). Combined organics were dried over Na₂SO₄, filtered through a short pad of silica and concentrated in vacuo. The residue was purified by low pressure liquid chromatography (silica gel, EtOAc/hexanes, gradient elution) affording (R)-4-chloro-1-(1-(5-cyanopyridin-3-yl)propyl)-1H-indole-5-carbonitrile (0.1024 g, 34% yield) as a gum which formed a tan solid upon trituration with Et₂O/hexanes: ¹H NMR (400 MHz, CDCl₃) δ 8.81 (d, J=1.1 Hz, 1H), 8.68 (d, J=1.8 Hz, 1H), 7.66-7.58 (m, 1H), 7.44 (d, J=3.4 Hz, 1H), 7.42 (d, J=8.8 Hz, 1H), 7.18 (d, J=8.5 Hz, 1H), 6.88 (d, J=3.1 Hz, 1H), 5.43 (dd, J=8.5, 6.9 Hz, 1H), 2.50-2.30 (m, 2H), 1.03 (t, J=7.3 Hz, 3H); MS (LCMS ES+) m/z 321 ([M+H]⁺, 55%), 362 ({[M+H]+MeCN}⁺, 100%).

Example 49

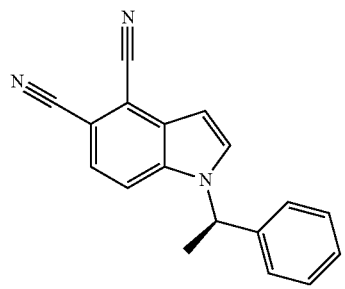 [SMILES: C[C@H](c1ccccc1)n1ccc2c(C#N)c(C#N)ccc21]

(R)-1-(1-Phenylethyl)-1H-indole-4,5-dicarbonitrile

An oven-dried vial was charged with 4-fluoro-3-((trimethylsilyl)ethynyl)phthalonitrile (Example 40C) (0.100 g, 0.413 mmol) and K₂CO₃ (0.057 g, 0.413 mmol) and sealed with a rubber septum. Anhyd NMP (2 mL) and (R)-1-phenylethanamine (0.053 mL, 0.413 mmol) were added via syringe and the mixture was stirred in a heating block at 60° C. under N₂. After 15 h, the mixture was cooled, quenched by addition of satd NH₄Cl, poured into water and extracted with EtOAc (×3). Combined organics were washed (water× 2, brine), dried over Na₂SO₄ and concentrated in vacuo. The residue was purified by low pressure liquid chromatography (silica gel, EtOAc/hexanes, gradient elution) affording (R)-1-(1-phenylethyl)-1H-indole-4,5-dicarbonitrile (0.0574 g, 51% yield) as a pale yellow solid: ¹H NMR (400 MHz, CDCl₃) δ 7.63 (d, J=3.3 Hz, 1H), 7.48 (dd, J=8.6, 0.7 Hz, 1H), 7.43 (d, J=8.7 Hz, 1H), 7.37-7.27 (m, 3H), 7.12-7.06 (m, 2H), 6.88 (dd, J=3.3, 0.7 Hz, 1H), 5.72 (q, J=7.1 Hz, 1H), 1.98 (d, J=7.0 Hz, 3H); MS (LCMS ES+) m/z 272 ([M+H]⁺, 5%), 289 (100%), 313 ({[M+H]+MeCN}, 23%), 335 ({[M+Na]+MeCN}, 22%).

Example 50

(R)-1-(1-(3-Cyanophenyl)ethyl)-1H-indole-4,5-dicarbonitrile

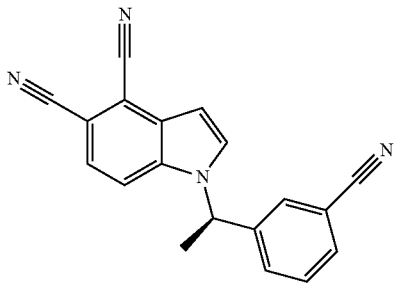 [SMILES: C[C@H](c1cccc(C#N)c1)n1ccc2c(C#N)c(C#N)ccc21]

An oven-dried vial was charged with 4-fluoro-3-((trimethylsilyl)ethynyl)phthalonitrile (Example 40C) (0.128 g, 0.528 mmol), (R)-3-(1-aminoethyl)benzonitrile (0.085 g, 0.581 mmol), and K₂CO₃ (0.080 g, 0.581 mmol) and sealed with a rubber septum. Anhyd NMP (3 mL) was added via syringe and the mixture was stirred in a heating block at 60° C. under N₂. After 3.5 h the septum was replaced with a PTFE-faced crimp top and the mixture was subjected to microwave heating (140° C.) for 20 min. Upon cooling, the mixture was poured into satd NaHCO₃ and extracted with EtOAc (×3). Combined organics were filtered (Whatman #2), washed (water, brine), dried over Na₂SO₄ and concentrated in vacuo. The residue was purified by low pressure liquid chromatography (silica gel, EtOAc/hexanes, gradient elution) affording (R)-1-(1-(3-cyanophenyl)ethyl)-1H-indole-4,5-dicarbonitrile (0.0705 g, 0.238 mmol, 45.0% yield) as a tan foam: $^1$H NMR (400 MHz, CDCl$_3$) δ 7.63 (d, J=3.4 Hz, 1H), 7.61 (dt, J=7.8, 1.3 Hz, 1H), 7.50-7.41 (m, 3H), 7.40 (t, J=1.8 Hz, 1H), 7.30-7.27 (m, 1H), 6.93 (dd, J=3.4, 0.7 Hz, 1H), 5.76 (q, J=7.1 Hz, 1H), 2.01 (d, J=7.1 Hz, 3H); MS (LCMS ES+) m/z 297 ([M+H]$^+$, 24%), 338 ({[M+H]+MeCN}$^+$, 100%).

Example 51

(R)-1-(1-(5-Cyanopyridin-3-yl)propyl)-1H-indole-4,5-dicarbonitrile

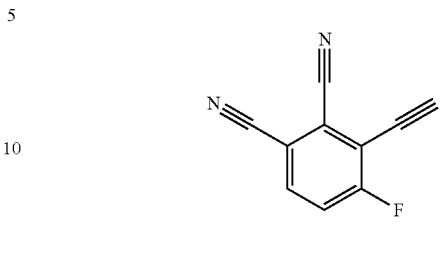

A. 3-Ethynyl-4-fluorophthalonitrile

To a solution of 4-fluoro-3-((trimethylsilyl)ethynyl)phthalonitrile (Example 40C) (0.302 g, 1.246 mmol) in anhyd THF (5 mL) was added a solution of TBAF in THF (1.246 mL, 1.246 mmol), dropwise. The resulting black mixture was stirred at rt under N₂ for 5 min. The mixture was poured into water and extracted with EtOAc (×3). Combined organics were washed (water, brine), dried over Na₂SO₄ and concentrated in vacuo. The residue was purified by low pressure liquid chromatography (silica gel, EtOAc/hexanes, gradient elution) affording 3-ethynyl-4-fluorophthalonitrile (0.0635 g, 30% yield) as a tan solid: $^1$H NMR (400 MHz, CDCl$_3$) δ 7.79 (dd, J=8.7, 4.7 Hz, 1H), 7.49 (dd, J=8.7, 8.0 Hz, 1H), 3.86 (s, 1H); MS (GCMS EI) m/z 170 ([M]$^+$, 100%).

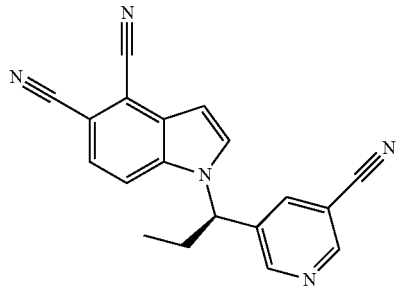 [SMILES: CC[C@H](c1cncc(C#N)c1)n1ccc2c(C#N)c(C#N)ccc21]

B. (R)-1-(1-(5-Cyanopyridin-3-yl)propyl)-1H-indole-4,5-dicarbonitrile

To a solution of (R)-5-(1-aminopropyl)nicotinonitrile hydrochloride (0.081 g, 0.411 mmol) in anhyd NMP (2.0 mL) was added DIEA (0.215 mL, 1.232 mmol) via syringe. The mixture was stirred 15 min and 3-ethynyl-4-fluorophthalonitrile (0.0635 g, 0.373 mmol) was added in one portion. The mixture was stirred at rt under N₂ for 36 h, poured into satd NaHCO₃ and extracted with EtOAc (×3). Combined organics were washed (water, brine), dried over Na₂SO₄ and concentrated in vacuo. The residue was dissolved in anhyd DMF (3 mL), CuI (0.036 g, 0.187 mmol) was added and the mixture was subjected to microwave heating (140° C.) for 30 min. The mixture was diluted with EtOAc and filtered through a pad of Celite. The filtrate was diluted 1:1 with heptane and concentrated in vacuo (3× heptane chase). The residue was purified by low pressure liquid chromatography (silica gel, EtOAc/hexanes, gradient elution) affording (R)-1-(1-(5-cyanopyridin-3-yl)propyl)-1H-indole-4,5-dicarbonitrile (0.0407 g, 0.131 mmol, 35.0%

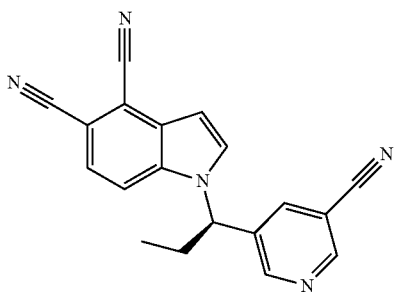 [SMILES: CC[C@H](c1cncc(C#N)c1)n1ccc2c(C#N)c(C#N)ccc21]

yield) as a yellow gum: ¹H NMR (400 MHz, CDCl₃) δ 8.83 (d, J=8.7 Hz, 1H), 8.69 (d, J=2.2 Hz, 1H), 7.66 (t, J=2.1 Hz, 1H), 7.63 (d, J=3.4 Hz, 1H), 7.53 (s, 2H), 7.00 (d, J=3.4 Hz, 1H), 5.50 (dd, J=8.7, 6.8 Hz, 1H), 2.53-2.34 (m, 2H), 1.03 (t, J=7.3 Hz, 3H); MS (LCMS ES+) m/z 312 ([M+H]⁺, 6%), 353 ({[M+H]+MeCN}⁺, 100%).

Example 52

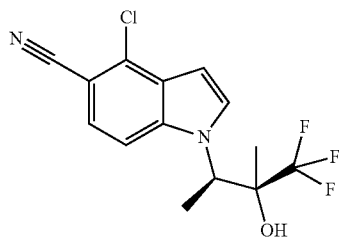 [SMILES: C[C@@H](n1ccc2c(Cl)c(C#N)ccc21)[C@](C)(O)C(F)(F)F]

4-Chloro-1-((2R,3S)-4,4,4-trifluoro-3-hydroxy-3-methylbutan-2-yl)-1H-indole-5-carbonitrile

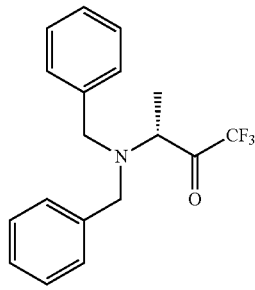 [SMILES: C[C@H](C(=O)C(F)(F)F)N(Cc1ccccc1)Cc1ccccc1]

A.
(R)-3-(Bibenzylamino)-1,1,1-trifluorobutan-2-one (R)-Methyl 2-(dibenzylamino)propanoate (made in a manner similar to Example 21E using commercially available (R)-methyl 2-aminopropanoate, hydrochloride (8.36 g, 29.5 mmol) was dissolved in toluene (15 mL) and treated with trimethyl(trifluoromethyl)silane (6.53 mL, 44.3 mmol). The mixture was cooled on an ice bath and tetrabutylammonium acetate (0.445 g, 1.48 mmol) was added. The reaction was left on the ice bath. TLC and LCMS after 1.5 h showed excellent conversion to a less polar (TLC) product. The mixture was quenched with sat. aq. NH₄Cl and extracted with EtOAc. The organic portions were dried over Na₂SO₄, filtered, and concentrated to a brown oil that was diluted with THF (40 mL) and then treated with 1N aqueous HCl (10 mL). The mixture was allowed to stir overnight. LCMS the next day showed the desired product along with a trace of the diaddition product. The mixture was neutralized with NaHCO₃ (saturated aqueous to pH ca. 9) and extracted with EtOAc. The combined organic portions were washed with sat NaHCO₃ followed by brine. The organic portion was then dried over Na₂SO₄, filtered, and concentrated to a dark amber oil that was chromatographed (ISCO, 220 g silica, hex/EtOAC; 0-30%; 230 and 254 nm) to afford the desired product as a bright yellow oil (6.83 g, 72%): MS (ESI): m/z 340 (M+H as hydrate).

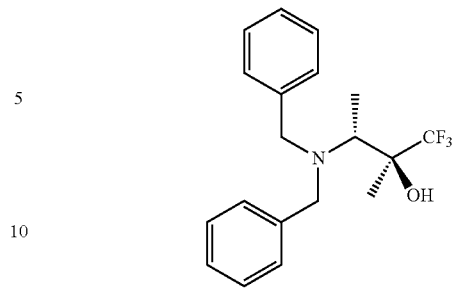

B. (2S,3R)-3-(Dibenzylamino)-1,1,1-trifluoro-2-methylbutan-2-ol (R)-3-(Dibenzylamino)-1,1,1-trifluorobutan-2-one (Example 52A) (3.41 g, 10.61 mmol) was dissolved in Et₂O (80 mL) and then cooled to ca. 0° C. (ice external temp) prior to the addition of MeMgI (7.07 mL, 3 M). Addition of the Grignard reagent caused the reaction to become heterogeneous. After stirring for 10 min, TLC indicated good conversion to a slightly less polar than sm product (a trace of what appeared to be sm remained), the mixture was quenched with sat. aq. NH₄Cl and extracted with EtOAc. The combined organic portions were dried over Na₂SO₄ and concentrated. The resulting bright yellow residue was purified by flash chromatography (ISCO, 80 g silica, 0% to 40% over 27 min. ca. 10 min ret time; hex/EtOAc) to afford the desired product as a bright yellow oil. TLC, LCMS, and NMR showed ca. 15-20% of the bis CF3 alcohol contaminating the desired product. A trace of the other diastereomer also existed. The material was concentrated and rechromatographed (straight CH₂Cl₂, 80 g SiO₂, 254/230 nm) to afford separation of the bis-CF3 alcohol and desired product (1.94 g, 54%). This material was used in its entirety for the debenzylation step: ¹H NMR (400 MHz, DMSO-d₆) δ 7.62-7.48 (m, 10H), 6.11 (s, 1H), 4.16 (d, J=13.6 Hz, 2H), 3.61 (d, J=13.7 Hz, 2H), 3.15 (q, J=6.8 Hz, 1H), 1.42-1.40 (m, 6H).

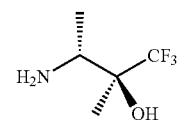

C.
(2S,3R)-3-Amino-1,1,1-trifluoro-2-methylbutan-2-ol (2S,3R)-3-(Dibenzylamino)-1,1,1-trifluoro-2-methylbutan-2-ol (Example 52B) (1.94 g, 5.75 mmol) was dissolved in MeOH (50 mL) and an then treated with the catalyst (0.612 g, 10% dry weight, 50% water). The reaction vessel was then purged with alternating vacuum and N₂ (7×). H₂ was introduced and then the vessel was purged again with vacuum alternated with H₂ (3×). The reaction vessel was then finally charged with H₂ (90 psi). The pressure was allowed to drop to ca. 80 psi and allowed to stay there overnight (H₂ uptake appeared to stop). After 15 h, the reaction was purged with N₂/vacuum cycles and the catalyst/carbon was removed by filtration through celite. The celite cake was rinsed with MeOH and the resulting filtrate was carefully concentrated to a white solid by rotavap followed by finishing the last part of the liquid volume with an N₂ blow down. The resulting grey solid/film was dissolved in CH₂Cl₂ and then filtered through a microfilter to remove remaining Pd/C. The resulting pale yellow filtrate was then blown down and exposed to light vacuum to afford a pale yellow solid (0.726 g, 80%) PMR of this material showed excellent purity and no remaining sm: $^1$H NMR (400 MHz, DMSO-d$_6$) δ 2.95 (q, J=6.7 Hz, 1H), 1.60 (bs, 2H), 1.13-1.11 (m, 3H), 0.96-0.94 (m, 3H).

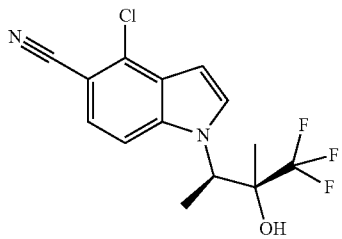 [SMILES: C[C@@H](n1ccc2c(Cl)c(C#N)ccc21)[C@](C)(O)C(F)(F)F]

D. 4-Chloro-1-((2R,3S)-4,4,4-trifluoro-3-hydroxy-3-methylbutan-2-yl)-1H-indole-5-carbonitrile 2-Chloro-4-fluoro-3-((trimethylsilyl)ethynyl)benzonitrile (Example 32B) (0.08 g, 0.318 mmol), (2S,3R)-3-amino-1,1,1-trifluoro-2-methylbutan-2-ol (Example 52C) (0.079 mg, 0.503 mmol), and Hunig's base (0.094 mL, 0.540 mmol) were combined in DMSO (1.0 mL) in a sealed tube and then heated to 100° C. Formation of the aniline intermediate was monitored by LCMS. Excellent conversion to this intermediate was realized after ca. 3 h of heating. The mixture was diluted with water and extracted with EtOAc. The combined organic portions were dried over Na₂SO₄ and concentrated to a brown oil. Further traces of DMSO were removed by high vac. The brown residue was diluted with NMP (ca. 1.0 mL) and then treated with KOtBu (0.095 mL, 1.0 M in THF). The resulting solution was then heated to 60° C. for 45 min at which time LCMS indicated formation of a very slightly less polar product. The UV trace of this product was far different from that of the aniline intermediate. The crude mixture was diluted with water and extracted with EtOAc. The combined organic portions were washed with water and brine and then dried over Na₂SO₄. Concentration afforded a thick brown oil that was purified by ISCO (24 g silica, hex/EtOAc up to 70%, detection at 254 and 230 nm) to afford the desired product as a pale yellow solid (0.078 g, 78%) in excellent purity: $^1$H NMR (400 MHz, DMSO-d$_6$) δ 7.79 (d, J=3.5 Hz, 1H), 7.71 (d, J=8.6 Hz, 1H), 7.57 (d, J=8.8 Hz, 1H), 6.68 (d, J=3.3 Hz, 1H), 6.50 (s, 1H), 5.03 (q, J=7.0 Hz, 1H), 1.51 (d, J=6.9 Hz, 3H), 1.37 (s, 3H); MS (ESI): m/z 317 (M+H).

Example 53

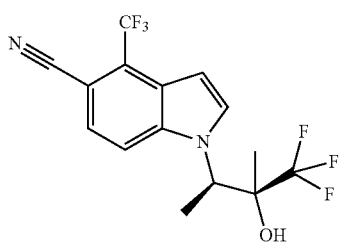

1-((2R,3S)-4,4,4-Trifluoro-3-hydroxy-3-methylbutan-2-yl)-4-(trifluoromethyl)-1H-indole-5-carbonitrile Synthesized in a manner similar to Example 52 using 4-fluoro-2-(trifluoromethyl)-3-((trimethylsilyl)ethynyl)benzonitrile (Example 21D): $^1$H NMR (400 MHz, DMSO-d$_6$) δ 8.05 (d, J=8.8 Hz, 1H), 7.94 (d, J=3.5 Hz, 1H), 7.76 (d, J=8.6 Hz, 1H), 6.78-6.76 (m, 1H), 6.54 (s, 1H), 5.15 (q, J=7.0 Hz, 1H), 1.54 (d, J=7.0 Hz, 3H), 1.39 (s, 3H); MS (ESI): m/z 351 (M+H).

Example 54

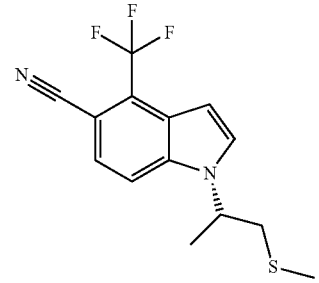

(S)-1-(1-(Methylthio)propan-2-yl)-4-(trifluoromethyl)-1H-indole-5-carbonitrile

Synthesized in a manner similar to Example 27D using (S)-1-(methylthio)propan-2-amine which was made in a manner similar to Example 27C: MS (ESI): m/z 299 (M+H).

Example 55

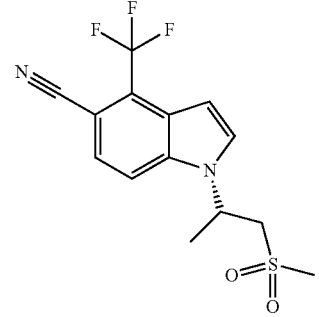

(S)-1-(1-(Methylsulfonyl)propan-2-yl)-4-(trifluoromethyl)-1H-indole-5-carbonitrile Synthesized in a manner similar to Example 27 using (S)-1-(1-(methylthio)propan-2-yl)-4-(trifluoromethyl)-1H-indole-5-carbonitrile: $^1$H NMR (400 MHz, DMSO-d$_6$) δ 8.16 (d, J=8.7 Hz, 1H), 8.12 (d, J=3.5 Hz, 1H), 7.81 (d, J=8.6 Hz, 1H), 6.85-6.84 (m, 1H), 5.40-5.35 (m, 1H), 4.01 (dd, J=14.6, 8.2 Hz, 1H), 3.83 (dd, J=14.9, 5.1 Hz, 1H), 2.76 (s, 3H), 1.59 (d, J=6.6 Hz, 3H); MS (ESI): m/z 331 (M+H).

Biological Section

Compounds of the current invention are modulators of the androgen receptor. Additionally, the compounds of the present invention may also prove useful as modulators of the glucocorticoid receptor, the mineralocorticoid receptor, and/or the progesterone receptor. Activity mediated through oxosteroid nuclear receptors was determined using the following in vitro and in vivo assays.

In Vitro Assays:

The following abbreviations and sources of materials are used

Fluormone PL Red—a commercially available PR fluoroprobe (Invitrogen, P2964)

Fluormone GS Red—a commercially available GR fluoroprobe (PanVera Corp, Product No P2894)

Fluormone AL Red—a commercially available AR fluoroprobe (Invitrogen, PV4294,)

MBP-hPR-LBD—maltose binding protein Purified human progesterone ligand binding domain (made in house)

GR—purified human glucocorticoid receptor (PanVera Corp, Product No P2812)

MBP-hAR-LBD—maltose binding protein Purified rat androgen ligand binding domain (made in house)

PR Screening Buffer—100 mM potassium phosphate (pH 7.4), 100 µG/ml bovine gamma globulin, 15% ethylene glycol, 10% glycerol with 2 mM CHAPS, 1 mM DTT added fresh and 4% DMSO added fresh (final of 5% DMSO in assay with 1% concentration coming from compound dispense)

AR Screening Buffer—50 mM Tris pH 7.5, 100 mM Ammonium Sulfate, 20% glycerol, 3% xyliltol with 5 mM Chaps, 2 mM DTT added fresh and 4% DMSO added fresh (final of 5% DMSO in assay with 1% concentration coming from compound dispense)

GR Screening Buffer—100 mM potassium phosphate (pH 7.4), 200 mM $Na_2MoO_2$, 1 mM EDTA, 20% DMSO (PanVera Corp Product No P2814) with GR stabilizing peptide (100 µM) (PanVera Corp Product No P2815)

DTT—dithiothreitol (PanVera Corp Product No P2325)

Discovery Analyst—is an FP reader

DMSO—dimethylsulphoxide

Progesterone Receptor Fluorescence Polarization Assay:

The progesterone receptor fluorescence polarization assay is used to investigate the interaction of the compounds with the progesterone receptor.

Compounds are added to the 384 well black low-volume plates to a final volume of 0.1 µL. DTT and DMSO are added to the chilled assay buffer just before beginning assay. Sufficient Fluormone PL Red and PR-LBD are defrosted on ice and added to the chilled buffer in a glass tube to give a final concentration of 2 nM and 8 nM, respectively. A volume of 10 µL of the assay mix is added to compound plates with a multidrop. The assay is allowed to incubate at 20-22° C. (room temp) for 2-3 hours. The plates are counted in a Discovery Analyst with suitable 535 nM excitation and 590 nM emission interference filters (Dichroic 561 nM). Compounds that interact with the PR result in a lower fluorescence polarization reading. Test compounds are dissolved and diluted in DMSO. Compounds are assayed in singlicate, a four parameter curve fit of the following form being applied $$y = \frac{a-d}{1+\left(\frac{x}{c}\right)^b} + d$$

where a is the minimum, b is the Hill slope, c is the $IC_{50}$ and d is the maximum. Maximum and minimum values are compared to adhesion in the absence of compound and in the presence of $10^{-5}$M progesterone. Data is presented as the mean $pIC_{50}$ with the standard error of the mean of n experiments.

Androgen Receptor Fluorescence Polarization Assay:

The androgen receptor fluorescence polarization assay is used to investigate the interaction of the compounds with the androgen receptor.

Compounds are added to the 384 well black low-volume plates to a final volume of 0.1 µL. DTT and DMSO are added to the chilled assay buffer just before beginning assay. Sufficient Fluormone AL Red and AR-LBD are defrosted on ice and added to the chilled buffer in a glass tube to give a final concentration of 1 nM and 100 nM, (for current batch) respectively. A volume of 10 µL of the assay mix is added to compound plates with a multidrop. The assay is allowed to incubate at 20° C. for 2-3 hours. The plates are counted in a Discovery Analyst with suitable 535 nM excitation and 590 nM emission interference filters (Dichroic 561 nM). Compounds that interact with the AR result in a lower fluorescence polarization reading. Test compounds are dissolved and diluted in DMSO. Compounds are assayed in singlicate, a four parameter curve fit of the following form being applied $$y = \frac{a-d}{1+\left(\frac{x}{c}\right)^b} + d$$

where a is the minimum, b is the Hill slope, c is the $IC_{50}$ and d is the maximum. Maximum and minimum values are compared to adhesion in the absence of compound and in the presence of $10^{-5}$M control compound, 2-((4-cyano-3-(trifluoromethyl)phenyl)(2,2,2-trifluoroethyl)amino)acetamide.

Data is presented as the mean $pIC_{50}$ with the standard error of the mean of n experiments. Results from selected examples are shown in Table 1.

TABLE 1

| Example | Binding $pIC_{50}$ | % Max | Std. error |
|---|---|---|---|
| 2 | 7.0 | 72 | 0.18 |
| 7 | 6.2 | 100 | n/a (n = 1) |
| 12 | 6.6 | 90 | 0.4 |
| 17 | 7.1 | 99 | 0.32 |
| 21 | 6.5 | 100 | 0.23 |
| 22 | 6.8 | 100 | 0.3 |
| 27 | 7.1 | 91 | 0.21 |
| 32 | 7.5 | 78 | 0.04 |
| 43 | 6.2 | 105 | 0.34 |
| 52 | 7.8 | 97 | 0.11 |

Glucocorticoid Receptor Fluorescence Polarization Assay

The glucocorticoid receptor fluorescence polarization assay is used to investigate the interaction of the compounds with the glucocorticoid receptor.

Compounds are added to the 384 well black plates to a final volume of 0.5 µL. Sufficient Fluormone GS Red and GR are defrosted on ice to give a final concentration of 1 nM and 4 nM, respectively. GR screening buffer is chilled to 4° C. prior to addition of DTT to give a final concentration of 1 mM. The Fluormone GS Red, and GR in GR Screening Buffer are added to compound plates to give a final volume of 10 µL. The assay is allowed to incubate at 4° C. for 12 hours. The plates are counted in a Discovery Analyst with suitable 535 nM excitation and 590 nM emission interference filters. Compounds that interact with the GR result in a lower fluorescence polarization reading. Test compounds are dissolved and diluted in DMSO. Compounds are assayed in singlicate, a four parameter curve fit of the following form being applied $$y = \frac{a-d}{1+\left(\frac{x}{c}\right)^b} + d$$

where a is the minimum, b is the Hill slope, c is the $EC_{50}$ and d is the maximum. Maximum and minimum values are compared to adhesion in the absence of compound and in the presence of $10^{-5}$M dexamethasone. Data is presented as the mean $pIC_{50}$ with the standard error of the mean of n experiments.

AR Functional Assay:

AR DNA Preparation

A plasmid containing an N-terminal truncation of the human AR gene was obtained from ATCC which was missing 154 residues from the N-terminus of the protein. The N-terminal region of the AR gene from a human liver cDNA library generated in-house, was cloned using PCR technique. The N-terminus and C-terminus pieces were PCR-ed together and subcloned in to the pSG5 vector at the BamHI site along with a Kozak sequence. The sequence differs from the published sequence in two regions of high variability within the receptor amongst published sequences. This clone has 1 additional glutamine residue (residue 79) and 3 additional glycine residues (position 475).

MMTV DNA Preparation pGL3-Basic Vector was digested with SmaI and XhoI. pMSG was digested with HindIII blunt ended and then digested with XhoI to excise the pMMTV-LTR. The pMMTV-LTR fragment was then ligated to the SmaI and XhoI sites of pGL3-Basic Vector. The resulting plasmid contains the MMTV promoter from position 26 to the XhoI site, followed by luciferase which is contained between the NcoI and SalI (position 3482) sites.

Assay Protocol

Monkey kidney CV-1 cells (ECACC No. 87032605) were transiently transfected with Fugene-6 reagent according to the manufacturer's protocol. Briefly, a T175 flask of CV-1 cells at a density of 80% confluency was transfected with 25 g of mix DNA and 751 of Fugene-6. The DNA mix (1.25 microg pAR, 2.5 microg pMMTV Luciferase and 18.75 microg pBluescript (Stratagene)) was incubated with Fugene in 5 ml OptiMEM-1 for 30 min and then diluted up to 20 ml in transfection media (DMEM containing 1% Hyclone, 2 mM L-Glutamine and 1% Pen/Strep) prior to addition to the cells. After 24 h, cells were washed with PBS, detached from the flask using 0.25% trypsin and counted using a Sysmex KX-21N. Transfected cells were diluted in assay media (DMEM containing 1% Hyclone, 2 mM L-Glutamine and 1% Pen/Strep) at 70 cells/microlitre l. 70 microlitres of suspension cells were dispensed to each well of white Nunc 384-well plates, containing compounds at the required concentration. After 24 h, 10 microlitres of Steady Glo were added to each well of the plates. Plates were incubated in the dark for 10 min before reading them on a Viewlux reader.

Analysis

All data was normalized to the mean of 16 high and 16 low control wells on each plate. A four parameter curve fit of the following form was then applied $$y = \frac{a-d}{1+\left(\frac{x}{c}\right)^b} + d$$

Where a is the minimum, b is the Hill slope, c is the XC50 and d is the maximum. Data is presented as the mean pXC50 with the standard deviation of the mean of n experiments.

The compounds shown in Examples 1 through 55 were tested in the AR functional assay and all had a $pIC_{50} \geq 5.01$ in the agonist mode of this assay.

Those of skill in the art will recognize that in vitro binding assays and cell-based assays for functional activity are subject to variability. Accordingly, it is to be understood that the values for the plCso's recited above are exemplary only.

Castrated Male Rat Model (ORX Rat)

The activity of the compounds of the present invention as modulators of the androgen receptor was investigated using a castrated male rat model (ORX) as described in C. D. Kockakian, *Pharmac. Therap. B*1(2), 149-177 (1975); C. Tobin and Y. Joubert, *Developmental Biology* 146, 131-138 (1991); J. Antonio, J. D. Wilson and F. W. George, *J Appl. Physiol.* 87(6) 2016-2019 (1999)) the disclosures of which herein are included by reference.

Androgens have been identified as playing important roles in the maintenance and growth of many tissues in both animals and humans. Muscles, like the levator ani and bulbocavernosus, and sexual accessory organs, such as the prostate glands and seminal vesicles have high expression levels of the androgen receptor and are known to respond quickly to exogenous androgen addition or androgen deprivation through testicular ablation. Castration produces dramatic atrophy of muscle and sexual accessory organs; whereas the administration of exogenous androgens to the castrated animal results in effective hypertrophy of these muscles and sexual accessory organs.

Although the levator ani muscle, also known as the dorsal bulbocavernosus, is not 'true skeletal muscle' and definitely sex-linked, it is reasonable to use this muscle to screen muscle anabolic activities of test compounds because of its androgen responsiveness and simplicity of removal.

Male Sprague-Dawley rats weighing 160-180 grams were used in the assay. The rats were singly caged upon receiving and throughout the study. Bilateral orchidectomies were performed in sterilized surgical conditions under isoflurane anesthesia. An anteroposterior incision was made in the scrotum. The testicles were exteriorized and the spermatic artery and vas deferens were ligated with 4.0 silk 0.5 cm proximal to the ligation site. The testicles then were removed by a surgical scissors distal to the ligation sites. The tissue stumps were returned to the scrotum, the scrotum and overlying skin were closed by a surgical stapler. The Sham-ORX rats underwent all procedures except ligation and scissors cutting. The rats were assigned randomly into study groups 7-10 days post surgery based on the body weight.

Dihydrotestosterone (DHT) and the standard SARM, S-22, (*J. Pharma. Exper. Thera.* Vol 315, p. 230) were used as a positive control (1-10 mg/kg s.c. for DHT and 0.1 to 3 mg/kg p.o. for S-22). Compounds of the current invention were administered subcutaneously or orally for 4-28 days. Alternatively, some compounds of the current invention were administered subcutaneously or orally for 7-49 days.

The rats were weighed daily and doses were adjusted accordingly. The general well being of the animal was monitored throughout the course of the study.

At the end of the study, the rats were euthanized in a $CO_2$ chamber. The ventral prostate glands (VP), seminal vesicles (SV), levator ani muscle (LA) and bulbocavernosus (BC) were carefully dissected. The tissues were blotted dry; the weights were recorded, and then saved for histological and molecular analysis. The VP and SV weights serve as androgenic indicators and LA and BC as anabolic indicators. The ratio of anabolic to androgenic activities was used to evaluate the test compounds. Serum luteinizing hormone (LH), follicle stimulating hormone (FSH) and other potential serum markers of anabolic activities were also analyzed.

In general, preferred compounds show levator ani hypertrophy and very little prostate stimulation.

The compounds shown in Examples 9, 20, 26, 27, 33, 51, 52, and 53 were tested in the castrated male rate model essentially as described above. Test compounds were employed in free or salt form. The compounds shown in Examples 9, 26, 27, 51, 52, and 53 showed favorable levator ani hypertrophy and spared the prostate. Compounds having favorable levator ani hypertrophy were defined as those that show a 30% or greater increase in levator ani weight when compared to vehicle-treated castrates and dosed orally at up to 10 mg/kg/day. Prostate sparing was defined as at least a 2:1 ratio of levator ani $ED_{50}$ to prostate $ED_{50}$. The $ED_{50}$ is defined as 50% of the maximum response above the vehicle treated castrate level. For shorter term studies (4-7 days), the maximum response is defined as the maximum response from positive control (DHT or standard SARM, S-22) treatment. For the longer term studies (7-49 days), the $ED_{50}$ is defined as 50% of the eugonadal state.

All research complied with the principles of laboratory animal care (NIH publication No. 85-23, revised 1985) and GlaxoSmithKline policy on animal use.

Those of skill in the art will recognize that in vivo animal model studies such as the castrated male rat model studies described above are subject to variability. Accordingly, it is to be understood that the values for favorable levator ani hypertrophy and prostate sparing recited above are exemplary only.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included within the scope of the appended claims.

That which is claimed:

1. A method of treating periodontal disease, wherein said method comprises administering the compound:

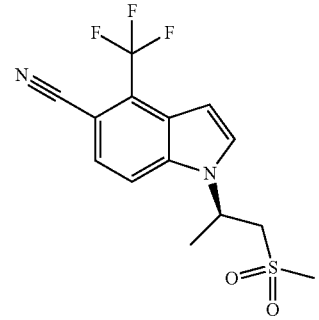 [SMILES: C[C@H](CS(C)(=O)=O)n1ccc2c(C(F)(F)F)c(C#N)ccc21]

to a human subject in need thereof.

2. The method according to claim 1, wherein 0.1-50 mgs of the compound is administered.

3. A method of treating chronic fatigue syndrome, wherein said method comprises administering the compound:

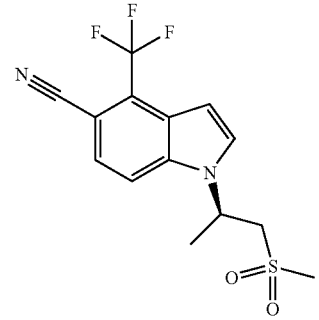 [SMILES: C[C@H](CS(C)(=O)=O)n1ccc2c(C(F)(F)F)c(C#N)ccc21]

to a human subject in need thereof.

4. The method according to claim 3, wherein 0.1-50 mgs of the compound is administered.

* * * * *